(12) United States Patent
Browning

(10) Patent No.: US 9,186,489 B2
(45) Date of Patent: *Nov. 17, 2015

(54) IMPLANTABLE DELIVERY DEVICE SYSTEM FOR DELIVERY OF A MEDICAMENT TO A BLADDER

(71) Applicant: Coloplast A/S, Humlebaek (DK)

(72) Inventor: James Browning, Glasgow (GB)

(73) Assignee: Coloplast A/S, Humlebaek (DK)

( * ) Notice: Subject to any disclaimer, the term of this patent is extended or adjusted under 35 U.S.C. 154(b) by 66 days.

This patent is subject to a terminal disclaimer.

(21) Appl. No.: 14/201,962

(22) Filed: Mar. 10, 2014

(65) Prior Publication Data
US 2014/0188042 A1 Jul. 3, 2014

Related U.S. Application Data

(63) Continuation of application No. 12/246,263, filed on Oct. 6, 2008, now Pat. No. 8,709,471, which is a continuation of application No. 10/550,699, filed as application No. PCT/GB2004/001390 on Mar. 26, 2004, now abandoned.

(30) Foreign Application Priority Data

Mar. 27, 2003 (GB) .................................. 0307082.8

(51) Int. Cl.
| | |
|---|---|
| A61F 6/06 | (2006.01) |
| A61F 2/00 | (2006.01) |
| A61M 37/00 | (2006.01) |
| A61M 31/00 | (2006.01) |
| A61F 6/14 | (2006.01) |
| A61K 9/00 | (2006.01) |

(52) U.S. Cl.
CPC ................ *A61M 31/007* (2013.01); *A61F 6/06* (2013.01); *A61F 6/142* (2013.01); *A61K 9/0036* (2013.01); *A61K 9/0039* (2013.01)

(58) Field of Classification Search
None
See application file for complete search history.

(56) References Cited

U.S. PATENT DOCUMENTS

| | | |
|---|---|---|
| 2,738,790 A | 3/1956 | Todt, Sr. et al. |
| 3,054,406 A | 9/1962 | Usher |
| 3,124,136 A | 3/1964 | Usher |
| 3,182,662 A | 5/1965 | Shirodkar |
| 3,311,110 A | 3/1967 | Singerman et al. |
| 3,384,073 A | 5/1968 | Van Winkle, Jr. |
| 3,472,232 A | 10/1969 | Earl |
| 3,580,313 A | 5/1971 | McKnight |
| 3,763,860 A | 10/1973 | Clarke |
| 3,789,828 A | 2/1974 | Schulte |
| 3,858,783 A | 1/1975 | Kapitanov et al. |
| 3,888,975 A | 6/1975 | Ramwell |
| 3,911,911 A | 10/1975 | Scommegna |
| 3,913,573 A | 10/1975 | Gutnick |
| 3,916,899 A | 11/1975 | Theeuwes et al. |
| 3,924,633 A | 12/1975 | Cook et al. |
| 3,993,058 A | 11/1976 | Hoff |
| 3,995,619 A | 12/1976 | Glatzer |
| 4,019,499 A | 4/1977 | Fitzgerald |
| 4,037,603 A | 7/1977 | Wendorff |
| 4,128,100 A | 12/1978 | Wendorff |
| 4,172,458 A | 10/1979 | Pereyra |
| 4,233,968 A | 11/1980 | Shaw, Jr. |
| 4,235,238 A | 11/1980 | Ogiu et al. |
| 4,246,660 A | 1/1981 | Wevers |
| 4,441,497 A | 4/1984 | Paudler |
| 4,444,933 A | 4/1984 | Columbus et al. |
| 4,509,516 A | 4/1985 | Richmond |
| 4,632,100 A | 12/1986 | Somers et al. |
| 4,633,873 A | 1/1987 | Dumican et al. |
| 4,646,731 A | 3/1987 | Brower |
| 4,655,221 A | 4/1987 | Devereux |
| 4,775,380 A | 10/1988 | Seedhom et al. |
| 4,857,041 A | 8/1989 | Annis et al. |
| 4,865,031 A | 9/1989 | O'Keeffe |
| 4,873,976 A | 10/1989 | Schreiber |

(Continued)

FOREIGN PATENT DOCUMENTS

| | | |
|---|---|---|
| DE | 2305815 A1 | 8/1974 |
| DE | 4220283 A1 | 12/1993 |

(Continued)

OTHER PUBLICATIONS

Penson and Raz, "Why Anti-incontinence Surgery Succeeds or Fails," Female Urology, 1996, Raz (ed.), W.B. Saunders Company, Chapter 41, pp. 435-442.
Pereyra et al., "Pubourethral Supports in Perspective: Modified Pereyra Procedure for Urinary Incontinence," Obstet Gynecol., 1982, 59:643-648.
Petros and Konsky, "Anchoring the midurethra restores bladder-neck anatomy and continence," The Lancet, 1999, 354:997-998.
Petros and Ulmsten, "An analysis of rapid pad testing and the history for the diagnosis of stress incontinence," Acta Obstet. Gynecol. Scand., 1992, 71:529-536.
Petros and Ulmsten, "An Anatomical Basis for Success and Failure of Female Incontinence Surgery," Scand. J. Urol. Nephrol., 1993, (Suppl. 3):55-60.

(Continued)

*Primary Examiner* — Jeffrey T Palenik

(74) *Attorney, Agent, or Firm* — Coloplast Corp., Coloplast A/S; Nick Baumann

(57) ABSTRACT

An implantable delivery device system for delivery of a medicament to a bladder includes a device body, a drug coating disposed over at least a portion of the device body, and an insertion tool. The device body includes a first end and a second end opposite of the first end, the first end having a first diameter and including a sharp tip for penetrating tissue and the second end having a second diameter and including a head portion. The second diameter is larger than the first diameter. The drug coating is disposed over a portion of the device body and is provided for treatment of an over active bladder. The insertion tool has a shaft located between a proximal end of the tool that includes a handle shaft and a distal end of the tool that is attachable to the head of the device.

14 Claims, 14 Drawing Sheets

(56) References Cited

U.S. PATENT DOCUMENTS

| | | |
|---|---|---|
| 4,920,986 A | 5/1990 | Biswas |
| 4,938,760 A | 7/1990 | Burton et al. |
| 5,013,292 A | 5/1991 | Lemay |
| 5,053,043 A | 10/1991 | Gottesman et al. |
| 5,085,661 A | 2/1992 | Moss |
| 5,112,344 A | 5/1992 | Petros |
| 5,123,428 A | 6/1992 | Schwarz |
| 5,149,329 A | 9/1992 | Richardson |
| 5,188,636 A | 2/1993 | Fedotov |
| 5,207,694 A | 5/1993 | Broome |
| 5,209,756 A | 5/1993 | Seedhom et al. |
| 5,250,033 A | 10/1993 | Evans et al. |
| 5,256,133 A | 10/1993 | Spitz |
| 5,259,835 A | 11/1993 | Clark et al. |
| 5,281,237 A | 1/1994 | Gimpelson |
| 5,328,077 A | 7/1994 | Lou |
| 5,336,239 A | 8/1994 | Gimpelson |
| 5,337,736 A | 8/1994 | Reddy |
| 5,342,376 A | 8/1994 | Ruff |
| 5,362,294 A | 11/1994 | Seitzinger |
| 5,368,595 A | 11/1994 | Lewis |
| 5,383,904 A | 1/1995 | Totakura et al. |
| 5,386,836 A | 2/1995 | Biswas |
| 5,403,328 A | 4/1995 | Shallman |
| 5,413,598 A | 5/1995 | Moreland |
| 5,434,146 A | 7/1995 | Labrie et al. |
| 5,439,467 A | 8/1995 | Benderev et al. |
| 5,456,711 A | 10/1995 | Hudson |
| 5,486,197 A | 1/1996 | Le et al. |
| 5,507,754 A | 4/1996 | Green et al. |
| 5,507,796 A | 4/1996 | Hasson |
| 5,520,700 A | 5/1996 | Beyar et al. |
| 5,522,896 A | 6/1996 | Prescott |
| 5,544,664 A | 8/1996 | Benderev et al. |
| 5,549,619 A | 8/1996 | Peters et al. |
| 5,562,685 A | 10/1996 | Mollenauer et al. |
| 5,562,689 A | 10/1996 | Green et al. |
| 5,569,273 A | 10/1996 | Titone et al. |
| 5,571,139 A | 11/1996 | Jenkins, Jr. |
| 5,591,163 A | 1/1997 | Thompson |
| 5,611,515 A | 3/1997 | Benderev et al. |
| 5,628,756 A | 5/1997 | Barker, Jr. et al. |
| 5,645,568 A | 7/1997 | Chervitz et al. |
| 5,647,836 A | 7/1997 | Blake, III et al. |
| 5,669,935 A | 9/1997 | Rosenman et al. |
| 5,683,349 A | 11/1997 | Makower et al. |
| 5,695,525 A | 12/1997 | Mulhauser et al. |
| 5,697,931 A | 12/1997 | Thompson |
| 5,697,978 A | 12/1997 | Sgro |
| 5,720,766 A | 2/1998 | Zang et al. |
| 5,749,884 A | 5/1998 | Benderev et al. |
| 5,766,221 A | 6/1998 | Benderev et al. |
| 5,807,403 A | 9/1998 | Beyar et al. |
| 5,816,258 A | 10/1998 | Jervis |
| 5,836,314 A | 11/1998 | Benderev et al. |
| 5,836,315 A | 11/1998 | Benderev et al. |
| 5,840,011 A | 11/1998 | Landgrebe et al. |
| 5,842,478 A | 12/1998 | Benderev et al. |
| 5,851,229 A | 12/1998 | Lentz et al. |
| 5,860,425 A | 1/1999 | Benderev et al. |
| 5,899,909 A | 5/1999 | Claren et al. |
| 5,904,692 A | 5/1999 | Steckel et al. |
| 5,919,232 A | 7/1999 | Chaffringeon et al. |
| 5,922,026 A | 7/1999 | Chin |
| 5,934,283 A | 8/1999 | Willem et al. |
| 5,935,122 A | 8/1999 | Fourkas et al. |
| 5,944,732 A | 8/1999 | Raulerson et al. |
| 5,954,057 A | 9/1999 | Li |
| 5,972,000 A | 10/1999 | Beyar et al. |
| 5,988,171 A | 11/1999 | Sohn et al. |
| 5,997,554 A | 12/1999 | Thompson |
| 6,010,447 A | 1/2000 | Kardjian |
| 6,030,393 A | 2/2000 | Corlew |
| 6,031,148 A | 2/2000 | Hayes et al. |
| 6,039,686 A | 3/2000 | Kovac |
| 6,042,534 A | 3/2000 | Gellman et al. |
| 6,042,536 A | 3/2000 | Tihon et al. |
| 6,042,583 A | 3/2000 | Thompson et al. |
| 6,048,306 A | 4/2000 | Spielberg |
| 6,048,351 A | 4/2000 | Gordon et al. |
| 6,050,937 A | 4/2000 | Benderev |
| 6,053,935 A | 4/2000 | Brenneman et al. |
| 6,056,688 A | 5/2000 | Benderev et al. |
| 6,068,591 A | 5/2000 | Bruckner et al. |
| 6,071,290 A | 6/2000 | Compton |
| 6,074,341 A | 6/2000 | Anderson et al. |
| 6,077,216 A | 6/2000 | Benderev et al. |
| 6,090,116 A | 7/2000 | D'Aversa et al. |
| 6,106,545 A | 8/2000 | Egan |
| 6,110,101 A | 8/2000 | Tihon et al. |
| 6,117,067 A | 9/2000 | Gil-Vernet |
| 5,633,286 B1 | 10/2000 | Chen |
| 6,159,207 A | 12/2000 | Yoon |
| 6,162,962 A | 12/2000 | Hinsch et al. |
| 6,168,611 B1 | 1/2001 | Rizvi |
| 6,190,401 B1 | 2/2001 | Green et al. |
| 6,197,036 B1 | 3/2001 | Tripp et al. |
| 6,200,330 B1 | 3/2001 | Benderev et al. |
| 6,221,005 B1 | 4/2001 | Bruckner et al. |
| 6,231,496 B1 | 5/2001 | Wilk et al. |
| 6,245,082 B1 | 6/2001 | Gellman et al. |
| 6,264,676 B1 | 7/2001 | Gellman et al. |
| 6,267,772 B1 | 7/2001 | Mulhauser et al. |
| 6,273,852 B1 | 8/2001 | Lehe et al. |
| 6,287,316 B1 | 9/2001 | Agarwal et al. |
| 6,292,700 B1 | 9/2001 | Morrison et al. |
| 6,302,840 B1 | 10/2001 | Benderev |
| 6,306,079 B1 | 10/2001 | Trabucco |
| 6,319,264 B1 | 11/2001 | Tormala et al. |
| 6,328,686 B1 | 12/2001 | Kovac |
| 6,328,744 B1 | 12/2001 | Harari et al. |
| 6,334,446 B1 | 1/2002 | Beyar |
| 6,352,553 B1 | 3/2002 | van der Burg et al. |
| 6,355,065 B1 | 3/2002 | Gabbay |
| 6,382,214 B1 | 5/2002 | Raz et al. |
| 6,387,041 B1 | 5/2002 | Harari et al. |
| 6,406,423 B1 | 6/2002 | Scetbon |
| 6,406,480 B1 | 6/2002 | Beyar et al. |
| 6,408,656 B1 | 6/2002 | Ory et al. |
| 6,418,930 B1 | 7/2002 | Fowler |
| 6,443,964 B1 | 9/2002 | Ory et al. |
| 6,461,332 B1 | 10/2002 | Mosel et al. |
| 6,475,139 B1 | 11/2002 | Miller |
| 6,478,727 B2 | 11/2002 | Scetbon |
| 6,478,791 B1 | 11/2002 | Carter et al. |
| 6,482,214 B1 | 11/2002 | Sidor, Jr. et al. |
| 6,491,703 B1 | 12/2002 | Ulmsten |
| 6,494,887 B1 | 12/2002 | Kaladelfos |
| 6,494,906 B1 | 12/2002 | Owens |
| 6,502,578 B2 | 1/2003 | Raz et al. |
| 6,506,190 B1 | 1/2003 | Walshe |
| 6,527,802 B1 | 3/2003 | Mayer |
| 6,530,943 B1 | 3/2003 | Hoepffner et al. |
| 6,544,273 B1 | 4/2003 | Harari et al. |
| 6,575,897 B1 | 6/2003 | Ory et al. |
| 6,575,998 B2 | 6/2003 | Beyar |
| 6,582,443 B2 | 6/2003 | Cabak et al. |
| 6,592,515 B2 | 7/2003 | Thierfelder et al. |
| 6,596,001 B2 | 7/2003 | Stormby et al. |
| 6,599,235 B2 | 7/2003 | Kovac |
| 6,599,318 B1 | 7/2003 | Gabbay |
| 6,599,323 B2 | 7/2003 | Melican et al. |
| 6,612,977 B2 | 9/2003 | Staskin et al. |
| 6,638,210 B2 | 10/2003 | Berger |
| 6,638,211 B2 | 10/2003 | Suslian et al. |
| 6,638,284 B1 | 10/2003 | Rousseau et al. |
| 6,641,524 B2 | 11/2003 | Kovac |
| 6,652,450 B2 | 11/2003 | Neisz et al. |
| 6,652,595 B1 | 11/2003 | Nicolo |
| 6,666,817 B2 | 12/2003 | Li |
| 6,669,706 B2 | 12/2003 | Schmitt et al. |
| 6,669,735 B1 | 12/2003 | Pelissier |
| 6,673,010 B2 | 1/2004 | Skiba et al. |
| 6,679,896 B2 | 1/2004 | Gellman et al. |

(56) References Cited

U.S. PATENT DOCUMENTS

| | | |
|---|---|---|
| 6,689,047 B2 | 2/2004 | Gellman |
| 6,691,711 B2 | 2/2004 | Raz et al. |
| 6,695,855 B1 | 2/2004 | Gaston |
| 6,702,827 B1 | 3/2004 | Lund et al. |
| 6,737,371 B1 | 5/2004 | Planck et al. |
| 6,755,781 B2 | 6/2004 | Gellman |
| 6,786,861 B1 | 9/2004 | Pretorius |
| 6,830,052 B2 | 12/2004 | Carter et al. |
| 6,884,212 B2 | 4/2005 | Thierfelder et al. |
| 6,911,003 B2 | 6/2005 | Anderson et al. |
| 6,932,759 B2 | 8/2005 | Kammerer et al. |
| 6,936,052 B2 | 8/2005 | Gellman et al. |
| 6,960,160 B2 | 11/2005 | Browning |
| 7,025,063 B2 | 4/2006 | Snitkin et al. |
| 7,070,556 B2 | 7/2006 | Anderson et al. |
| 7,070,558 B2 | 7/2006 | Gellman et al. |
| 7,094,199 B2 | 8/2006 | Petros et al. |
| 7,112,171 B2 | 9/2006 | Rocheleau et al. |
| 7,112,210 B2 | 9/2006 | Ulmsten et al. |
| 7,140,956 B1 | 11/2006 | Korovin et al. |
| 7,156,858 B2 | 1/2007 | Schuldt Hempe et al. |
| 7,204,802 B2 | 4/2007 | De Leval |
| 7,229,404 B2 | 6/2007 | Bouffier |
| 7,288,063 B2 | 10/2007 | Petros et al. |
| 7,290,410 B2 | 11/2007 | Meneghin et al. |
| 7,297,102 B2 | 11/2007 | Smith et al. |
| 7,326,213 B2 | 2/2008 | Benderev et al. |
| 7,347,812 B2 | 3/2008 | Mellier |
| 7,387,634 B2 | 6/2008 | Benderev |
| 7,395,822 B1 | 7/2008 | Burton et al. |
| 7,410,460 B2 | 8/2008 | Benderev |
| 7,500,945 B2 | 3/2009 | Cox et al. |
| 7,517,313 B2 | 4/2009 | Thierfelder et al. |
| 7,527,633 B2 | 5/2009 | Rioux |
| 7,559,885 B2 | 7/2009 | Merade et al. |
| 7,594,921 B2 | 9/2009 | Browning |
| 7,601,118 B2 | 10/2009 | Smith et al. |
| 7,611,454 B2 | 11/2009 | De Leval |
| 7,614,258 B2 | 11/2009 | Cherok et al. |
| 7,621,864 B2 | 11/2009 | Suslian et al. |
| 7,628,156 B2 | 12/2009 | Astani et al. |
| 7,673,631 B2 | 3/2010 | Astani et al. |
| 7,686,760 B2 | 3/2010 | Anderson et al. |
| 7,691,050 B2 | 4/2010 | Gellman et al. |
| 7,713,188 B2 | 5/2010 | Bouffier |
| 7,722,528 B2 | 5/2010 | Arnal et al. |
| 7,740,576 B2 | 6/2010 | Hodroff et al. |
| 7,766,926 B2 | 8/2010 | Bosley, Jr. et al. |
| 7,789,821 B2 | 9/2010 | Browning |
| 7,794,385 B2 | 9/2010 | Rosenblatt |
| 7,815,662 B2 | 10/2010 | Spivey et al. |
| 7,927,342 B2 | 4/2011 | Rioux |
| 7,975,698 B2 | 7/2011 | Browning |
| 7,981,022 B2 | 7/2011 | Gellman et al. |
| 8,007,430 B2 | 8/2011 | Browning |
| 8,016,741 B2 | 9/2011 | Weiser et al. |
| 8,016,743 B2 | 9/2011 | Maroto |
| 8,047,983 B2 | 11/2011 | Browning |
| 8,092,366 B2 | 1/2012 | Evans |
| 8,118,727 B2 | 2/2012 | Browning |
| 8,118,728 B2 | 2/2012 | Browning |
| 8,123,673 B2 | 2/2012 | Browning |
| 8,128,554 B2 | 3/2012 | Browning |
| 8,162,818 B2 | 4/2012 | Browning |
| 8,167,785 B2 | 5/2012 | Browning |
| 8,182,412 B2 | 5/2012 | Browning |
| 8,182,413 B2 | 5/2012 | Browning |
| 8,215,310 B2 | 7/2012 | Browning |
| 8,273,011 B2 | 9/2012 | Browning |
| 8,449,450 B2 | 5/2013 | Browning |
| 8,454,492 B2 | 6/2013 | Browning |
| 8,469,877 B2 | 6/2013 | Browning |
| 8,512,223 B2 | 8/2013 | Browning |
| 8,574,148 B2 | 11/2013 | Browning |
| 8,668,635 B2 | 3/2014 | Browning |
| 2001/0000533 A1 | 4/2001 | Kovac |
| 2001/0018549 A1 | 8/2001 | Scetbon |
| 2001/0039423 A1 | 11/2001 | Skiba et al. |
| 2001/0049467 A1 | 12/2001 | Lehe et al. |
| 2001/0049538 A1 | 12/2001 | Trabucco |
| 2001/0051815 A1 | 12/2001 | Esplin |
| 2001/0053916 A1 | 12/2001 | Rioux |
| 2002/0005204 A1 | 1/2002 | Benderev et al. |
| 2002/0007222 A1 | 1/2002 | Desai |
| 2002/0022841 A1 | 2/2002 | Kovac |
| 2002/0028980 A1 | 3/2002 | Thierfelder et al. |
| 2002/0042658 A1 | 4/2002 | Tyagi |
| 2002/0049503 A1 | 4/2002 | Milbocker |
| 2002/0052612 A1 | 5/2002 | Schmitt et al. |
| 2002/0052654 A1 | 5/2002 | Darois et al. |
| 2002/0055748 A1 | 5/2002 | Gellman et al. |
| 2002/0058959 A1 | 5/2002 | Gellman |
| 2002/0068948 A1 | 6/2002 | Stormby et al. |
| 2002/0072694 A1 | 6/2002 | Snitkin et al. |
| 2002/0077526 A1 | 6/2002 | Kammerer et al. |
| 2002/0078964 A1 | 6/2002 | Kovac et al. |
| 2002/0082619 A1 | 6/2002 | Cabak et al. |
| 2002/0083949 A1 | 7/2002 | James |
| 2002/0091298 A1 | 7/2002 | Landgrebe |
| 2002/0091373 A1 | 7/2002 | Berger |
| 2002/0099258 A1 | 7/2002 | Staskin et al. |
| 2002/0099259 A1 | 7/2002 | Anderson et al. |
| 2002/0099260 A1 | 7/2002 | Suslian et al. |
| 2002/0103542 A1 | 8/2002 | Bilbo |
| 2002/0107430 A1 | 8/2002 | Neisz et al. |
| 2002/0107525 A1 | 8/2002 | Harari et al. |
| 2002/0115906 A1 | 8/2002 | Miller |
| 2002/0119177 A1 | 8/2002 | Bowman et al. |
| 2002/0128670 A1 | 9/2002 | Ulmsten et al. |
| 2002/0138025 A1 | 9/2002 | Gellman et al. |
| 2002/0147382 A1 | 10/2002 | Neisz et al. |
| 2002/0151762 A1 | 10/2002 | Rocheleau et al. |
| 2002/0151909 A1 | 10/2002 | Gellman et al. |
| 2002/0151910 A1 | 10/2002 | Gellman et al. |
| 2002/0156487 A1 | 10/2002 | Gellman et al. |
| 2002/0156488 A1 | 10/2002 | Gellman et al. |
| 2002/0161382 A1 | 10/2002 | Neisz et al. |
| 2002/0183588 A1 | 12/2002 | Fierro |
| 2002/0188169 A1 | 12/2002 | Kammerer et al. |
| 2003/0004395 A1 | 1/2003 | Therin |
| 2003/0009181 A1 | 1/2003 | Gellman et al. |
| 2003/0023136 A1 | 1/2003 | Raz et al. |
| 2003/0023137 A1 | 1/2003 | Gellman |
| 2003/0023138 A1 | 1/2003 | Luscombe |
| 2003/0036676 A1 | 2/2003 | Scetbon |
| 2003/0050530 A1 | 3/2003 | Neisz et al. |
| 2003/0065246 A1 | 4/2003 | Inman et al. |
| 2003/0065402 A1 | 4/2003 | Anderson et al. |
| 2003/0069469 A1 | 4/2003 | Li |
| 2003/0078468 A1 | 4/2003 | Skiba et al. |
| 2003/0100954 A1 | 5/2003 | Schuldt Hempe et al. |
| 2003/0130670 A1 | 7/2003 | Anderson et al. |
| 2003/0149440 A1 | 8/2003 | Kammerer et al. |
| 2003/0171644 A1 | 9/2003 | Anderson et al. |
| 2003/0176875 A1 | 9/2003 | Anderson et al. |
| 2003/0191360 A1 | 10/2003 | Browning |
| 2003/0199732 A1 | 10/2003 | Suslian et al. |
| 2003/0212305 A1 | 11/2003 | Anderson et al. |
| 2003/0220538 A1 | 11/2003 | Jacquetin |
| 2004/0029478 A1 | 2/2004 | Planck et al. |
| 2004/0034373 A1 | 2/2004 | Schuldt Hempe et al. |
| 2004/0039453 A1 | 2/2004 | Anderson et al. |
| 2004/0059356 A1 | 3/2004 | Gingras |
| 2004/0097974 A1 | 5/2004 | De Leval |
| 2004/0106847 A1 | 6/2004 | Benderev |
| 2004/0144395 A1 | 7/2004 | Evans et al. |
| 2004/0172048 A1 | 9/2004 | Browning |
| 2004/0231678 A1 | 11/2004 | Fierro |
| 2004/0243166 A1 | 12/2004 | Odermatt et al. |
| 2004/0249240 A1 | 12/2004 | Goldmann et al. |
| 2004/0249373 A1 | 12/2004 | Gronemeyer et al. |
| 2004/0249397 A1 | 12/2004 | Delorme et al. |
| 2004/0249473 A1 | 12/2004 | Delorme et al. |
| 2005/0000524 A1 | 1/2005 | Cancel et al. |

(56) References Cited

U.S. PATENT DOCUMENTS

| | | |
|---|---|---|
| 2005/0004576 A1 | 1/2005 | Benderev |
| 2005/0080317 A1 | 4/2005 | Merade |
| 2005/0107805 A1 | 5/2005 | Bouffier et al. |
| 2005/0240076 A1 | 10/2005 | Neisz et al. |
| 2005/0277806 A1 | 12/2005 | Cristalli |
| 2005/0278037 A1 | 12/2005 | Delorme et al. |
| 2005/0283040 A1 | 12/2005 | Greenhalgh |
| 2006/0025649 A1 | 2/2006 | Smith et al. |
| 2006/0025783 A1 | 2/2006 | Smith et al. |
| 2006/0041185 A1 | 2/2006 | Browning |
| 2006/0058578 A1 | 3/2006 | Browning |
| 2006/0089524 A1 | 4/2006 | Chu |
| 2006/0089525 A1 | 4/2006 | Mamo et al. |
| 2006/0130848 A1 | 6/2006 | Carey |
| 2006/0205995 A1 | 9/2006 | Browning |
| 2006/0264698 A1 | 11/2006 | Kondonis et al. |
| 2007/0015953 A1 | 1/2007 | MacLean |
| 2007/0020311 A1 | 1/2007 | Browning |
| 2007/0032695 A1 | 2/2007 | Weiser |
| 2007/0032881 A1 | 2/2007 | Browning |
| 2007/0059199 A1 | 3/2007 | Labuschagne |
| 2007/0149555 A1 | 6/2007 | Kase et al. |
| 2007/0219606 A1 | 9/2007 | Moreci et al. |
| 2008/0021263 A1 | 1/2008 | Escude et al. |
| 2008/0161837 A1 | 7/2008 | Toso et al. |
| 2008/0167518 A1 | 7/2008 | Burton et al. |
| 2008/0196729 A1 | 8/2008 | Browning |
| 2008/0200751 A1 | 8/2008 | Browning |
| 2009/0123522 A1 | 5/2009 | Browning |
| 2009/0137862 A1 | 5/2009 | Evans et al. |
| 2009/0171377 A1 | 7/2009 | Intoccia et al. |
| 2009/0221868 A1 | 9/2009 | Evans |
| 2009/0287229 A1 | 11/2009 | Ogdahl |
| 2010/0022822 A1 | 1/2010 | Walshe |
| 2010/0056856 A1 | 3/2010 | Suslian et al. |
| 2010/0113869 A1 | 5/2010 | Goldman |
| 2010/0130814 A1 | 5/2010 | Dubernard |
| 2010/0198002 A1 | 8/2010 | O'Donnell |
| 2010/0222794 A1 | 9/2010 | Browning |
| 2010/0256442 A1 | 10/2010 | Ogdahl et al. |
| 2010/0274074 A1 | 10/2010 | Khamis et al. |
| 2010/0280308 A1 | 11/2010 | Browning |
| 2010/0298630 A1 | 11/2010 | Wignall |
| 2011/0021868 A1 | 1/2011 | Browning |
| 2011/0034759 A1 | 2/2011 | Ogdahl et al. |
| 2011/0105833 A1 | 5/2011 | Gozzi et al. |
| 2011/0124954 A1 | 5/2011 | Ogdahl et al. |
| 2011/0124956 A1 | 5/2011 | Mujwid et al. |
| 2011/0201872 A1 | 8/2011 | Browning |
| 2011/0230705 A1 | 9/2011 | Browning |
| 2011/0230708 A1 | 9/2011 | Browning |
| 2011/0230709 A1 | 9/2011 | Browning |
| 2011/0237865 A1 | 9/2011 | Browning |
| 2011/0237866 A1 | 9/2011 | Browning |
| 2011/0237867 A1 | 9/2011 | Browning |
| 2011/0237868 A1 | 9/2011 | Browning |
| 2011/0237869 A1 | 9/2011 | Browning |
| 2011/0237870 A1 | 9/2011 | Browning |
| 2011/0237873 A1 | 9/2011 | Browning |
| 2011/0237874 A1 | 9/2011 | Browning |
| 2011/0237875 A1 | 9/2011 | Browning |
| 2011/0237876 A1 | 9/2011 | Browning |
| 2011/0237877 A1 | 9/2011 | Browning |
| 2011/0237878 A1 | 9/2011 | Browning |
| 2011/0237879 A1 | 9/2011 | Browning |
| 2011/0238095 A1 | 9/2011 | Browning |
| 2011/0245594 A1 | 10/2011 | Browning |
| 2011/0282136 A1 | 11/2011 | Browning |
| 2012/0143000 A1 | 6/2012 | Browning |
| 2012/0149977 A1 | 6/2012 | Browning |
| 2012/0199133 A1 | 8/2012 | Browning |
| 2014/0039244 A1 | 2/2014 | Browning |
| 2014/0039247 A1 | 2/2014 | Browning |
| 2014/0039248 A1 | 2/2014 | Browning |
| 2014/0051917 A1 | 2/2014 | Browning |

FOREIGN PATENT DOCUMENTS

| | | |
|---|---|---|
| DE | 4304353 A1 | 4/1994 |
| DE | 10019604 C2 | 6/2002 |
| EP | 0009072 A1 | 4/1980 |
| EP | 0024781 B1 | 8/1984 |
| EP | 0024780 B1 | 10/1984 |
| EP | 0248544 B1 | 4/1991 |
| EP | 0139286 B1 | 8/1991 |
| EP | 0470308 A1 | 2/1992 |
| EP | 0557964 A1 | 9/1993 |
| EP | 0632999 A1 | 1/1995 |
| EP | 0650703 A1 | 5/1995 |
| EP | 0706778 A1 | 4/1996 |
| EP | 1093758 A1 | 4/2001 |
| EP | 0719527 B1 | 8/2001 |
| EP | 0643945 B1 | 3/2002 |
| EP | 1060714 B1 | 8/2006 |
| EP | 1274370 B1 | 9/2006 |
| EP | 1296614 B1 | 9/2006 |
| EP | 0797962 B2 | 9/2009 |
| FR | 1274370 A | 10/1961 |
| FR | 2712177 A1 | 5/1995 |
| FR | 2732582 A1 | 10/1997 |
| FR | 2735015 A1 | 2/1998 |
| FR | 2811218 E | 11/2000 |
| FR | 2787990 A1 | 4/2001 |
| GB | 0378288 A | 8/1932 |
| GB | 2353220 A | 2/2001 |
| RU | 2187251 C1 | 8/2002 |
| RU | 2196518 C2 | 1/2003 |
| SU | 1225547 A1 | 4/1986 |
| SU | 1342486 A1 | 10/1987 |
| SU | 1475607 A1 | 4/1989 |
| WO | WO9100714 A1 | 1/1991 |
| WO | WO9317635 A1 | 9/1993 |
| WO | WO9319678 A2 | 10/1993 |
| WO | WO9533454 A1 | 12/1995 |
| WO | WO9603091 A1 | 2/1996 |
| WO | WO9606567 A1 | 3/1996 |
| WO | WO9713465 A1 | 4/1997 |
| WO | WO9722310 A2 | 6/1997 |
| WO | WO9743982 A1 | 11/1997 |
| WO | WO9819606 A1 | 5/1998 |
| WO | WO9835606 A2 | 8/1998 |
| WO | WO9835616 A1 | 8/1998 |
| WO | WO9835632 A1 | 8/1998 |
| WO | WO9857590 A1 | 12/1998 |
| WO | WO9916381 A1 | 4/1999 |
| WO | WO9952450 A1 | 10/1999 |
| WO | WO9959477 A1 | 11/1999 |
| WO | WO0007520 A1 | 2/2000 |
| WO | WO0013601 A1 | 3/2000 |
| WO | WO0015141 A1 | 3/2000 |
| WO | WO0018319 A1 | 4/2000 |
| WO | WO0038784 A1 | 7/2000 |
| WO | WO0057812 A1 | 10/2000 |
| WO | WO0064370 A1 | 11/2000 |
| WO | WO0074594 A1 | 12/2000 |
| WO | WO0074613 A1 | 12/2000 |
| WO | WO0074633 A2 | 12/2000 |
| WO | WO0106951 A1 | 2/2001 |
| WO | WO0126581 A1 | 4/2001 |
| WO | WO0139670 A1 | 6/2001 |
| WO | WO0145589 A1 | 6/2001 |
| WO | WO0152729 A2 | 7/2001 |
| WO | WO0156499 A1 | 8/2001 |
| WO | WO0180773 A1 | 11/2001 |
| WO | WO0202031 A1 | 1/2002 |
| WO | WO0226108 A2 | 4/2002 |
| WO | WO0228312 A1 | 4/2002 |
| WO | WO0230293 A1 | 4/2002 |
| WO | WO0232284 A2 | 4/2002 |
| WO | WO0232346 A1 | 4/2002 |
| WO | WO0234124 A2 | 5/2002 |
| WO | WO0239890 A2 | 5/2002 |
| WO | WO02060371 A1 | 8/2002 |
| WO | WO02065921 A1 | 8/2002 |
| WO | WO02065944 A1 | 8/2002 |

(56) References Cited

FOREIGN PATENT DOCUMENTS

| WO | WO02069781 A2 | 9/2002 |
|---|---|---|
| WO | WO02071953 A2 | 9/2002 |
| WO | WO02078548 A1 | 10/2002 |
| WO | WO02078552 A1 | 10/2002 |
| WO | WO02078568 A1 | 10/2002 |
| WO | WO02078571 A2 | 10/2002 |
| WO | WO02098340 A1 | 12/2002 |
| WO | WO03002027 A1 | 1/2003 |
| WO | WO03013392 A1 | 2/2003 |
| WO | WO03057074 A2 | 7/2003 |
| WO | WO03022260 B1 | 10/2003 |
| WO | WO03086205 A2 | 10/2003 |
| WO | WO03092546 A2 | 11/2003 |
| WO | WO03094781 A1 | 11/2003 |
| WO | WO2004002370 A1 | 1/2004 |
| WO | WO2004002379 A1 | 1/2004 |
| WO | WO2004004600 A1 | 1/2004 |
| WO | WO2004012626 A1 | 2/2004 |
| WO | WO2004098461 A2 | 11/2004 |
| WO | WO2005018494 A1 | 3/2005 |
| WO | WO2005112842 A1 | 12/2005 |
| WO | WO2006015031 A2 | 2/2006 |
| WO | WO2006015042 A1 | 2/2006 |
| WO | WO2006136625 A1 | 12/2006 |
| WO | WO2007059199 A2 | 5/2007 |
| WO | WO2007149555 A2 | 12/2007 |
| WO | WO2008007086 A2 | 1/2008 |
| WO | WO2008018494 A1 | 2/2008 |

OTHER PUBLICATIONS

Petros and Ulmsten, "An Integral Theory of Female Urinary Incontinence," Acta Obstet. Gynecol. Scand., 1990, 69 (Suppl.153):7-31.
Petros and Ulmsten, "Bladder Instability in Women: A Premature Activation of the Micturition Reflex," Neurourology and Urodynamics, 1993, 12:235-239.
Petros and Ulmsten, "Cough Transmission Ratio: An Indicator of Suburethral Vaginal Wall Tension Rather than Urethral Closure?" Acta Obstet. Gynecol. Scand., 1990, 69(Suppl. 153):37-38.
Petros and Ulmsten, "Cure of Stress Incontinence by Repair of External Anal Sphincter," Acta. Obstet. Gynecol Scand., 1990, 69(Suppl. 153):75.
Petros and Ulmsten, "Cure of Urge Incontinence by the Combined Intravaginal Sling and Tuck Operation," Acta Obstet. Gynecol. Scand., 1990, 69(Suppl. 153)61-62.
Petros and Ulmsten, "Further Development of the Intravaginal Slingplasty Procedure—IVS III—(with midline "tuck")," Scand. J. Urol. Nephrol., 1993, Suppl. 153:69-71.
Petros and Ulmsten, "Non Stress Non Urge Female Urinary Incontinence—Diagnosis and Cure: A Preliminary Report," Acta Obstet. Gynecol. Scand., 1990, 69(Suppl. 153):69-70.
Petros and Ulmsten, "Part I: Theoretical, Morphological, Radiographical Correlations and Clinical Perspective," Scand. J. Urol. Nephrol., 1993, Suppl. 153:5-28.
Petros and Ulmsten, "Part II:The Biomechanics of Vaginal Tissue and supporting Ligaments with Special Relevance to the Pathogenesis of Female Urinary Incontinence," Scand. J. Urol. Nephrol., 1993, Suppl. 153:29-40.
Petros and Ulmsten, "Part III: Surgical Principles Deriving from the Theory," Scand. J. Urol. Nephrol., 1993, Suppl. 153:41-52.
Petros and Ulmsten, "Part IV: Surgical Applications of the Theory—Development of the Intravaginal Sling Plasty (IVS) Procedure," Scand. J. Urol. Nephrol., 1993, Suppl. 153:53-54.
Petros and Ulmsten, "Pinch Test for Diagnosis of Stress Urinary Incontinence," Acta Obstet. Gynecol. Scand., 1990, 69(Suppl. 153):33-35.
Petros and Ulmsten, "Pregnancy Effects on the Intravaginal Sling Operation," Acta Obstet. Gynecol. Scand., 1990, 69 (Suppl.153):77-78.
Petros and Ulmsten, "The Combined Intravaginal Sling and Tuck Operation. An Ambulatory Procedure for Cure of Stress and Urge Incontinence," Acta Obstet. Gynecol. Scand., 1990, 69(Suppl. 153):53-59.
Petros and Ulmsten, "The Development of the Intravaginal Slingplasty Procedure: IVS II—(with bilateral "tucks")," Scand. J. Urol. Nephrol., 1993, Suppl. 153:61-67.
Petros and Ulmsten, "The Free Graft Procedure for Cure of the Tethered Vagina Syndrome," Scand. J. Urol. Nephrol., 1993, Suppl. 153:85-87.
Petros and Ulmsten, "The Further Development of the Intravaginal Slingplasty Procedure: IVS IV—(with "double-breasted" unattached vaginal flap repair and "free" vaginal tapes)," Scand. J. Urol. Nephrol., 1993, Suppl. 153:73-79.
Petros and Ulmsten, "The Intravaginal Slingplasty Procedure: IVS VI—further development of the "double-breasted" vaginal flap repair—attached flap," Scand. J. Urol. Nephrol., 1993, Suppl. 153:81-84.
Petros and Ulmsten, "The Posterior Fornix Syndrome: A Multiple Symptom Complex of Pelvin Pain and Abnormal Urinary Symptoms Deriving from Laxity in the Posterior Fornix of Vagina," Scand. J. Urol. Nephrol., 1993, Suppl. 153:89-93.
Petros and Ulmsten, "The Role of a Lax Posterior Vaginal Fornix in the Causation of Stress and Urgency Symptoms: a Preliminary Report," Acta Obstet. Gynecol. Scand., 1990, 69(Suppl. 153):71-73.
Petros and Ulmsten, "The Tethered Vagina Syndrome, Post Surgical Incontinence and I-Plasty Operation for Cure," Acta Obstet. Gynecol Scand., 1990, 69(Suppl.153):63-67.
Petros and Ulmsten, "The Tuck Procedure: A Simplified Vaginal Repair for Treatment of Female Urinary Incontinence," Acta Obstet. Gynecol. Scand., 1990, 69(Suppl.153):41-42.
Petros and Ulmsten, "Urethral Pressure Increase on Effort Originates From Within the Urethra, and Continence From Musculovaginal Closure," Neurourology and Urodynamics, 1995, 14:337-350.
Petros et al., "The Autogenic Ligament Procedure: A Technique for Planned Formation of an Artificial Neo-Ligament," Acta Obstet. Gynecol. Scand., 1990, 69(Suppl. 153):43-51.
Petros, "Development of Generic Models for Ambulatory Vaginal Surgery—a Preliminary Report," Int. Urogynecol. J., 1998, 9:19-27.
Product Monograph for Aris Transobturator Tape for the Treatment of Female Stress Urinary Incontinence, 2004, 40 pages.
Rackley et al., "Tension-free Vaginal Tape and Percutaneous Vaginal Tape Sling Procedures," Techniques in Urology, 2001, 7(2):90-100.
Rackley, "Synthetic slings: Five steps for successful placement—Follow these steps to insert Transvaginal/Percutaneous slings using vaginal approach alone," Urology Times, 2000, 28:46-49.
Raz et al., "Urological Neurology and Urodynamics," J. Urol., 1992, 148:845-850.
Raz, "Modified Bladder Neck Suspension for Female Stress Incontinence," Urology, 1981, 17(1):82-85.
Richardson et al., "Delayed Reaction to the Dacron Buttress Used in Urethropexy," J. Reproductive Med., 1984, 29 (9):689-692.
Ridley, "Appraisal of the Goebell-Frangenheim-Stoeckel sling procedure," Am. J. Obstet. Gynecol., 1966, 95 (5):714-721.
Schumpelick, V. et at., "Minimized polypropylene mesh for preperitoneal net plasty (PNP) of incisional hernias," Chirurg 70:422-430 (1999).
Shaw, W., "An Operation for the Treatment of Stress Incontinence," Br. Med. J. 1949:1070-1073.
Sheiner et al., "An unusual complication of obturator foramen arterial bypass," J. Cardiovasc. Surg., 1969, 10 (4):324-328.
Sirls and Leach, "Use of Fascia Lata for Pubovaginal Sling," Female Urology, 1996, Raz (ed.). W.B. Saunders Company, Chapter 32, pp. 376-381.
Sloan and Barwin, "Stress Incontinence of Urine: A Retrospective Study of the Complications and Late Results of Simple Suprapubic Suburethral Fascial Slings," J. Urol., 1973, 110:533-536.
Spencer et al., "A Comparison of Endoscopic Suspension of the Vesical Neck with Suprapubic Vesicourethropexy for Treatment of Stress Urinary Incontinence," J. Urol., 1987, 137:411-415.
Spinosa, JP et al., Transobturator surgery for female stress incontinence: a comparative anatomical study of outside-in vs. inside-out techniques, BJU Intl., 100(5), pp. 1097-1102 (Nov. 2007).
Stamey, "Endoscopic Suspension of the Vesical Neck for Urinary Incontinence in Females," Annals of Surgery, 1980, 192(4):465-471.
Stanton, "Suprapubic Approaches for Stress Incontinence in Women," J. Am. Geriatrics Soc., 1990, 38(3):348-351.

(56) References Cited

OTHER PUBLICATIONS

Staskin et al., "The Gore-tex sling procedure for female sphincteric incontinence: indications, technique, and results," World J. Urol., 1997, 15:295-299.
Stothers et al., "Anterior Vaginal Wall Sling," Female Urology, 1996, Raz (ed.), W.B. Saunders Company, Chapter 35, pp. 395-398.
Surgimesh Sling Treatment of Incontinence http://www.aspide.com Mar. 4, 2011.
Jeffcoate, "The Results of the Aldridge Sling Operation for Stress Incontinence," The Journal of Obstetrics and Gynaecology of the British Empire, 1956, 63:36-39.
Jeter, "The Social Impact of Urinary Incontinence," Female Urology, Raz (ed.), W. B. Saunders Company, 1996, Chapter 7, pp. 80-86.
Karram and Bhatia, "Patch Procedure: Modified Transvaginal Fascia Lata Sling for Recurrent or Severe Stress Urinary Incontinence," Obstet Gynecol., 1990, 75:461-463.
Kerdiles et al., "Bypass via the Obturator Foramen in Reconstructive Arterial Surgery of the Lower Extremities," Ann. Chir. Thorac. Cardio-Vasc., 1974, 13(4):335-341.
Kerr and Staskin, "The Use of Artificial Material for Sling Surgery in the Treatment of Female Stress Urinary Incontinence," Female Urology, 1996, Raz (ed.), W.B. Saunders Company, Chapter 33, pp. 382-391.
Kersey, "The gauze hammock sling operation in the treatment of stress incontinence," Br. J. Obstet. Gynecol., 1983, 90:945-949.
Klinge et al., "Functional and Morphological Evaluation of a Low-Weight, Monofilament Polypropylene Mesh for Hernia Repair," Journal of Biomaterial Material Research, Jan. 24, 2002, pp. 129-137.
Klinge, U. et al., "Influence of polyglactin-coating on functional and morphological parameters of polypropylene-mesh modifications for abnormal wall repair," Biomaterials 20 (1999), pp. 613-623.
Klinge, U. et al., "Modified Mesh for Hernia Repair that is Adapted to the Physiology of the Abdominal Wall," Eur J Surg 164:951-960 (1998).
Klinge, U. et al., "Pathophysiology of the abdominal wall," Der Chirurg, (1996),67: 229-233.
Klosterhalfen, B, et al., "Functional and morphological evaluation of different polypropylene-mesh modifications for abdominal wall repair," Biomaterials 19:2235-2246 (1998).
Klosterhalfen, B. et al., "Morphological correlation of the functional mechanics of the abdominal wall after mesh implantation," Langenbecks Arch Chir 382:87-94 (1997).
Klutke et al., "The Anatomy of Stress Incontinence: Magnetic Resonance Imaging of the Female Bladder Neck and Urethra," J. Urol., 1990, 143:563-566.
Klutke et al., "Transvaginal Bladder Neck Suspension to Cooper's Ligament: A Modified Pereyra Procedure," Obstet. Gynecol., 1996, 88:294-297.
Korda et al., "Experience with Silastic Slings for Female Urinary Incontinence," Aust. NZ J. Obstet. Gynaecol., 1989, 29:150-154.
Kovac and Cruikshank, "Pubic Bone Suburethral Stabilization Sling for Recurrent Urinary Incontinence," Obstet. Gynecol., 1997, 89:624-627.
Kovac and Cruikshank, "Pubic bone suburethral stabilization sling: a long-term cure for SUI?" Contemporary OB/GYN, 1998, 43(2):51-72.
Kovac, "Follow-up of the Pubic Bone Suburethral Stabilization Sling Operation for Recurrent Urinary Incontinence (Kovac Procedure)," J. Pelvic Surgery, 1999, 5(3):156-160.
Lazarevski, M.B., Suburethral Duplication of the Vaginal Wall—An Original Operation for Urinary Stress Incontinence in Women, 6 Int'l Urogynecol. J. 73-79 (1995).
Leach et al., "Female Stress Urinary Incontinence Clinical Guidelines Panel Summary Report on Surgical Management of Female Stress Urinary Incontinence," J. Urol., 1997, 158:875-880.
Leach, "Bone Fixation Technique for Transvaginal Needle Suspension," Urology, 1988, 31(5):388-390.
Lichtenstein et al., "The Tension-Free Hernioplasty," Am. J. Surgery, 1989, 157:188-193.

Lipton, S. and Estrin, J., "A Biomechanical Study of the Aponeurotic Iguinal Hernia Repair," Journal of the American College of Surgeons, Jun. 1994, vol. 178, pp. 595-599.
Loughlin et al., "Review of an 8-Year Experience with Modifications of Endoscopic Suspension of the Bladder Neck for Female Stress Urinary Incontinence," J. Urol., 1990, 143:44-45.
Maher, Surgical Management of Anterior Vaginal Wall Prolapse: An Evidence Based Literature Review, 2006.
Mahoney and Whelan, "Use of Obturator Foramen in Iliofemoral Artery Grafting: Case Reports," Annals of Surgery, 1966, 163(2):215-220.
Marshall et al., "The Correction of Stress Incontinence by Simple Vesicourethral Suspension," J. Urol., 2002, 168:1326-1331.
McGuire and Gormley, "Abdominal Fascial Slings," Female Urology, 1996, Raz (ed.), W.B. Saunders Company, Chapter 31, pp. 369-375.
McGuire and Lytton, "Pubovaginal Sling Procedure for Stress Incontinence," J. Urol., 1978, 119:82-84.
McGuire et al., "Experience with Pubovaginal Slings for Urinary Incontinence at the University of Michigan," J. Urol., 1987, 138:525-526.
McGuire, "Abdominal Procedures for Stress Incontinence," Urologic Clinics of North America, 1985, 12(2):285-290.
McIndoe et al., "The Aldridge Sling Procedure in the Treatment of Urinary Stress Incontinence," Aust. NZ J. Obstet. Gynaecol., 1987, 27:238-239.
McKiel, Jr. et al., "Marshall-Marchetti Procedure: Modification," J. Urol., 1966, 96:737-739.
Miklos, Mini Sling Incontinence Treatment—Vagina Plastic Surgery, http://www.miklosandmoore.com/mini_sling.php, Feb. 28, 2011.
MiniArc Single-Incision Sling http://www.americanmedicalsystems.com Mar. 4, 2011.
Moir, "The Gauze-Hammock Operation," The Journal of Obstetrics and Gynaecology of the British Commonwealth, 1968, 75(1):1-9.
Monseur, J., Anatomie Chirurgicale: Les Ligaments Du Perinee Feminin, Sep. 4, 2008.
Moore et al. "Single-Center Retrospective Study of the Technique, Safety, and 12 Month Efficacy or the MiniArc™ Single Incision Sling: A New Minimally Invasive Procedure for Treatment of Female SUI" [Online] 2009, 18, pp. 175-181.
Morgan et al., "The Marlex sling operation for the treatment of recurrent stress urinary incontinence: A 16-year review," Am. J. Obstet. Gynecol., 1985, 151:224-226.
Morgan, "A sling operation, using Marlex polypropylene mesh, for treatment of recurrent stress incontinence," Am. J. Obstet. Gynecol., 1970, 106(3):369-376.
Narik and Palmrich, "A simplified sling operation suitable for routine use," Am. J. Obstet. Gynecol., 1962, 84:400-405.
Nichols, "The Mersilene Mesh Gauze-Hammock for Severe Urinary Stress Incontinence," Obstet. Gynecol., 1973, 41 (1):88-93.
Nicita, Giulio, (1998), "A New Operation for Genitourinary Prolapse," The Journal of Urology, 160:741-745.
Nickel et al., "Evaluation of a Transpelvic Sling Procedure With and Without Colpolsuspension for Treatment of Female Dogs With Refractory Urethral Sphincter Mechanism Incompetence," Veterinary Surgery, 1998, 27:94-104.
Norris et al., "Use of Synthetic Material in Sling Surgery: A Minimally Invasive Approach," J. Endocrinology, 1996, 10 (3):227-230.
Novak, "Abdonomovaginal Techniques," Gynecological Surgical Technique, 1977, Piccin Editore, Padua, 5 pages.
O'Donnell, "Combined Raz Urethral Suspension and McGuire Pubovaginal Sling for Treatment of Complicated Stress Urinary Incontinence," J. Arkansas Medical Society, 1992, 88(8):389.
Parra and Shaker, "Experience with a Simplified Technique for the Treatment of Female Stress Urinary Incontinence," British Journal of Urology, 1990, 66:615-617.
Pelosi II and Pelosi III, "New transobturator sling reduces risk of injury," OBG Management, 2003, pp. 17-37.
Pelosi III and Pelosi, "Pubic Bone Suburethral Stabilization Sling: Laparoscopic Assessment of a Transvaginal Operation for the Treatment of Stress Urinary Incontinence," Journal of Laparoendoscopic & Advanced Surgical Techniques, 1999, 9(1):45-50.

(56) References Cited

OTHER PUBLICATIONS

Abdel-fattah, Mohamed et al. Evaluation of transobturator tapes (E-TOT) study: randomised prospective single-blinded study comparing inside-out vs. outside-in transobturator tapes in management of urodynamic stress incontinence: Short term outcomes, European Journal of Obstetrics & Gynecology and Reproductive Biology (2009).
Aldridge, "Transplantation of Fascia for Relief of Urinary Stress Incontinence," Am. J. Obstet. Gynecol., 1942, 44:398-411.
Araki et al., "The Loop-Loosening Procedure for Urination Difficulties After Stamey Suspension of the Vesical Neck," J Urol., 1990, 144:319-323.
Asmussen and Ulmsten, "Simultaneous Urethro-Cystometry with a New Technique," Scand. J. Urol. Nephrol., 1976, 10:7-11.
Beck and McCormick, "Treatment of Urinary Stress Incontinence with Anterior Colporrhaphy," Obstetrics and Gynecology, 1982, 59(3):271-274.
Benderev, "A Modified Percutaneous Outpatient Bladder Neck Suspension System," J. Urol., 1994, 152:2316-2320.
Benderev, "Anchor Fixation and Other Modifications of Endoscopic Bladder Neck Suspension," Urology, 1992, 40 (5):409-418.
Bergman and Elia, "Three surgical procedures for genuine stress incontinence: Five-year follow-up of a prospective randomized study," Am. J. Obstet. Gynecol., 1995, 173:66-71.
Blaivas and Jacobs, "Pubovaginal Fascial Sling for the Treatment of Complicated Stress Urinary Incontinence," J. Urol., 1991, 145:1214-1218.
Blaivas and Salinas, "Type III Stress Urinary Incontinence: Importance of Proper Diagnosis and Treatment," American College of Surgeons Surgical Forum, 1984, 70.sup.th Annual Clinical Congress, San Francisco, CA, vol. XXXV, pp. 473-474.
Botros, Cystocele and Rectocele Repair: More Success With Mesh? Jun. 2006.
Bryans, "Marlex gauze hammock sling operation with Cooper's ligament attachment in the management of recurrent urinary stress incontinence," Am. J. Obstet. Gynecol., 1979, 133(3):292-294.
Burch, "Urethrovaginal fixation to Cooper's ligament for correction of stress incontinence, cystocele, and prolapse," Am. J. Obstet. Gynecol., 1961, 81(2):281-290.
Priority document for GB Application No. 0025068.8, filed Oct. 12, 2000, 38 pages.
Priority document for GB Application No. 0208359.0, filed Apr. 11, 2002, 50 pages.
Priority document for GB Application No. 0411360.1, filed May 21, 2004, 31 pages.
Chen, Biologic Grafts and Synthetic Meshes in Pelvic Reconstructive Surgery, Jun. 2007.
Choe and Staskin, "Gore-Tex Patch Sling: 7 Years Later," Urology, 1999, 54:641-646.
Chopra et al., "Technique of Rectangular Fascial Sling," Female Urology, 1996, Raz (ed.), W.B. Saunders Company, Chapter 34, pp. 392-394.
Dargent, D. et al., Pose d'un ruban sous uretral oblique par voie obturatrice dans le traitement de L'incontinence urinary feminine [English "Insertion of a transobturator oblique suburethral sling in the treatment of female urinary incontinence"], Gynecol. Obstet. Ferril. 14, pp. 576-582 (2002) [including English translation at the beginning of document].
Das and Palmer, "Laparoscopic Colpo-Suspension," J. Urol., 1995, 154:1119-1121.
de Leval, J., "Novel Surgical Technique for the Treatment of Female Stress Urinary Continence: Transobturator Vaginal Tape Inside-Out," European Urology, 2003, 44:724-730.
DeBord, James R., (1998), "The Historical Development of Prosthetics in Hernia Surgery," Surgical Clinics of North America, 78(6): 973-1006.
Decter, "Use of the Fascial Sling for Neurogenic Incontinence: Lessons Learned," J. Urol., 1993, 150:683-686.
Delmore, E. et al., La bandelette trans-obturatrice: Un procede mini-invasif pour traiter l'incontinence urinaire d'effort de la femme, Progres en Urologie, vol. 11, pp. 1306-1313 (2001) [including English translation at the beginning of document].
deTayrac, et al. Prolapse repair by vaginal route using . . . Int. Urogynecol. J. (published online May 13, 2006).
Dwyer, Transvaginal repair of anterior and posterior compartment prolapse with Atrium polypropylene mesh, BJOG: An International Journal of Obstetrics & Gynaecology, Aug. 2004.
Enzelsberger et al., "Urodynamic and Radiologic Parameters Before and After Loop Surgery for Recurrent Urinary Stress Incontinence," Acta Obstet. Gynecol. Scand., 1990, 69:51-54.
Eriksen et al., "Long-Term Effectiveness of the Burch Colposuspension in Female Urinary Stress Incontinence," Acta Obstet. Gynecol. Scand., 1990, 69:45-50.
Falconer et al., "Clinical Outcome and Changes in Connective Tissue Metabolism After Intravaginal Slingplasty in Stress Incontinent Women," Int. Urogynecol. J., 1996, 7:133-137.
Falconer et al., "Influence of Different Sling Materials on Connective Tissue Metabolism in Stress Urinary Incontinent Women," Int. Urogynecol. J., 2001, (Suppl. 2):S19-S23.
Gilja et al., "A Modified Raz Bladder Neck Suspension Operation (Transvaginal Burch)," J. Urol., 1995, 153:1455-1457.
Gittes and Loughlin, "No-Incision Pubovaginal Suspension for Stress Incontinence," J. Urol., 1987, 138:568-570.
Gruss, "The Obturator Bypass. Indications. Techniques. Outcomes," Chirurgie, 1971, 97:220-226.
Guida and Moore, "The Surgeon At Work. Obturator Bypass Technique," Surgery, Gynecology & Obstetrics, 1969, pp. 1307-1315.
Handa et al., "Banked Human Fascia Lata for the Suburethral Sling Procedure: A Preliminary Report," Obstet. Gynecol., 1996, 88:1045-1049.
Hardiman, et al. Cystocele repair using polypropylene mesh. Br. J. Obstet. Gynaecol. 107: 825-26 (2000).
Henriksson and Ulmsten, "A urodynamic evaluation of the effects of abdominal urethrocystopexy and vaginal sling urethroplasty in women with stress incontinence," Am. J. Obstet. Gynecol., 1978, 131:77-82.
Hodgkinson and Kelly, "Urinary Stress Incontinence in the Female. III. Round-ligament technique for retropubic suspension of the urethra," Obstet. Gynecol., 1957, 10:493-499.
Hohenfellner and Petri, "Sling Procedures," Surgery of Female Incontinence, 2nd edition, SpringerVeriag, pp. 105-113, 1986.
Holschneider et al., "The Modified Pereyra Procedure in Recurrent Stress Urinary Incontinence: A 15-Year Review," Obstet. Gynecol., 1994, 83:573-578.
Horbach et al., "A Suburethral Sling Procedure with Polytetrafluoroethylene for the Treatment of Genuine Stress Incontinence in Patients with Low Urethral Closure Pressure," Obstet. Gynecol., 1988, 71:648-652.
Horbach, "Suburethral Sling Procedures," Urogynecology and Urodynamics-Theory and Practice, 1996, Williams & Wilkins, pp. 569-579.
Ingelman-Sundberg and Ulmsten, "Surgical Treatment of Female Urinary Stress Incontinence," Contr. Gynec. Obstet., 1983, 10:51-69.
International Preliminary Examination Report issued in PCT/GB01/04554, completed Nov. 22, 2002, 6 pages.
International Search Report and Written Opinion issued in PCT/GB2004/001390, mailed Sep. 3, 2004, 12 pages.
International Search Report for PCT/GB2009/050174, mailed Jun. 24, 2009.
International Search Report issued in PCT/GB01/04554, mailed Jan. 29, 2002, 3 pages.
International Search Report issued in PCT/GB2007/002589, mailed Jan. 22, 2008, 5 pages.
Jacquetin, Bernard, "2. Utilisation du "TVT" dans la chirurgie de l'incontinence urinaire feminine", J. Gynecol. Obstet. Biol. Reprod. 29: 242-47 (2000).
Ulmsten and Petros, "Intravaginal Slingplasty (IVS): An Ambulatory Surgical Procedure for Treatment of Female Urinary Incontinence," Scand. J. Urol. Nephrol., 1995, 29:75-82.
Ulmsten et al., "A three-year follow up of tension free vaginal tape for surgical treatment of female stress urinary incontinence," Br. J. Obstet. Gynecol., 1999, 106:345-350.

(56) References Cited

OTHER PUBLICATIONS

Ulmsten et al., "An Ambulatory Surgical Procedure Under Local Anesthesia for Treatment of Female Urinary Incontinence," Int. Urogynecol. J., 1996, 7:81-86.
Ulmsten et al., "Different Biochemical Composition of Connective Tissue in Continent and Stress Incontinent Women," Acta Obstet. Gynecol. Scand., 1987, 66:455-457.
Ulmsten et al., "The unstable female urethra," Am. J. Obstet. Gynecol., 1982, 144:93-97.
Ulmsten, "Female Urinary Incontinence—A Symptom, Not a Urodynamic Disease. Some Theoretical and Practical Aspects on the Diagnosis and Treatment of Female Urinary Incontinence," Int. Urogynecol. J., 1995, 6:2-3.
Ulstem et al., "A Multicenter Study of Tension-Free Vaginal Tape (TVT) for Surgical Treatment of Stress Urinary Incontinence," Int. Urogynecol. J., 1998, 9:210-213.
U.S. Appl. No. 13/149,994, filed Jun. 1, 2011.
U.S. Appl. No. 10/106,086, filed Mar. 25, 2002.
U.S. Appl. No. 11/199,061, filed Aug. 8, 2005.
U.S. Appl. No. 60/279,794, filed Mar. 29, 2001.
U.S. Appl. No. 60/302,929, filed Jul. 3, 2001.
U.S. Appl. No. 60/307,836, filed Jul. 25, 2001.
U.S. Appl. No. 60/322,309, filed Sep. 14, 2001.
U.S. Appl. No. 60/362,806, filed Mar. 7, 2002.
U.S. Appl. No. 60/380,797, filed May 14, 2002.
U.S. Appl. No. 60/393,969, filed Jul. 5, 2002.
U.S. Appl. No. 60/402,007, filed Aug. 8, 2002.
U.S. Appl. No. 60/414,865, filed Sep. 30, 2002.
Webster and Kreder, "Voiding Dysfunction Following Cystourethropexy: Its Evaluation and Management," J. Urol., 1990, 144:670-673.
Weidemann, Small Intestinal Submucosa for Pubourethral Sling Suspension for the Treatment of Stress Incontinence: First Histopathological Results in Humans, Jul. 2004.
Winter, "Peripubic Urethropexy for Urinary Stress Incontinence in Women," Urology, 1982, 20(4):408-411.
Woodside and Borden, "Suprapubic Endoscopic Vesical Neck Suspension for the Management of Urinary Incontinence in Myelodysplastic Girls," J. Urol., 1986, 135:97-99.
Written Opinion for PCT/GB2009/050174, mailed Jun. 24, 2009.
Written Opionion issued in PCT/GB2007/002589, mailed Jan. 22, 2008, 5 pages.
Zacharin and Hamilton, "Pulsion Enterocele: Long-Term Results of an Abdominoperineal Technique," Obstet. Gynecol., 1980, 55(2):141-148.
Zacharin, "The suspensory mechanism of the female urethra," J. Anat., 1963, 97(3):423-427.

IMPLANTABLE DELIVERY DEVICE SYSTEM FOR DELIVERY OF A MEDICAMENT TO A BLADDER

This invention relates to a medicament delivery device and a method of delivering a medicament. In particular, but not exclusively the present invention relates to a device and a method for providing an implant in the uterine myometrium (in females) or prostate gland (in males) and the delivery of medicament to the pelvic area and organs thereof, for example the bladder, peritoneum, and in females the vulva, vagina, fallopian tubes, ovaries and uterus and then into the bloodstream.

There are many drugs which may be administered to the human and animal body for the prevention or treatment of disease. Different types of drugs call for different ways of administering the drug to the human or animal body.

Currently, most benign gynaecological conditions, for example endometriosis or fibroids, are treated using traditional methods of medicament or drug delivery, primarily oral and intravenous administration. Where possible, drugs are provided in pill, capsule, powder or liquid form for oral administration to a human or animal. The drug is then absorbed by the digestive system and will usually enter the blood stream via the liver to take effect. However, far from all drugs are suitable for such administration. For example, many drugs are broken down by the digestion process and destroyed before they can enter the blood stream. This problem is caused by what is commonly referred to as the "first pass liver metabolism" of the human or animal body, i.e. the process by which all substances absorbed by the digestive system must pass through the liver into the blood stream. Therefore, to provide sufficient drug to the female reproductive organs, relatively large doses of a drug are required. These large doses can cause side effects.

To avoid or minimise the problem of the first pass liver metabolism, drugs can be provided by injection, for example drugs desired to take an instant effect in the blood stream of a human or animal body may be injected into a vein, i.e. intravenously. Alternatively, drugs may be injected into muscle tissue from which the drug is absorbed more slowly into the blood stream. Drugs for injection into muscle tissue may, for example, be provided in an oily base which helps to regulate the rate of absorption. However, injections can be painful and difficult, particularly injections into muscle tissue, and can lead to tissue damage where frequent injections are required on a long term basis, e.g. of insulin for diabetics.

Other types of drug delivery include nasal sprays for administration of drugs to the nasal tissues and lungs; patches, such as the Nicorette® patch, for the application of Nicotine, or Ortho Evra, a contraceptive patch which releases oestrogen/progesterone through the skin; and lotions or ointments for topical application, i.e. directly to an affected part of the body.

However, these alternative types of drug delivery means can suffer from disadvantages. For example, skin patches can cause skin irritation, suffer from disattachment and cause cosmetic issues.

Although the above drug delivery methods are useful for particular types of drugs and medicines, with the exception of intramuscular depot injections, they are unable to provide therapeutic levels of drugs over a long term, e.g. weeks, months and years rather than days, without repeated application by the patient, a career, physician or general practitioner.

For application of drugs on a long term basis, various implants have been developed. One such type of implant may be inserted under the skin and have a mechanism for slowly releasing a drug into the blood stream of the human or animal in which it is implanted. For example, Norplant® or Implanon® comprise an implant having small capsules or rods which slowly release levonorgestrel or etonorgestrel into the blood stream to provide a contraceptive effect for women. Norplant® can be effective for up to five years.

However, these implants inserted under the skin suffer from a number of disadvantages. In particular the insertion of such an implant is painful, can cause significant bruising and discomfort at the implant site and requires local anaesthesia on both insertion and removal. In addition, as such implants are placed under the skin in for example the arm, they can be visible and cause discolouration of the skin. Furthermore, as the arm contains many different types of tissue and planes of tissue, movement of the implant along or through these tissue planes can occur. This can mean the implant moves to locations other than where it was placed during insertion which can lead to complications for the patient, in particular during removal of the implant. Difficulties with the Norplant® implant has led to it being withdrawn from clinical use.

For gynaecological conditions, long term local drug delivery through the vagina or endometrium is useful to deliver drugs to the pelvic region and organs thereof for example to the bladder, peritoneum, vulva, vagina, ovaries and uterus.

Current delivery means include vaginal creams, gels, intrauterine devices (contraceptive coils, IUD or IUCD) and vaginal rings or tampons.

Intrauterine devices (IUDs) are placed in the endometrial cavity typically to provide a contraceptive effect. For example, Leiras (Schering AG) market an intrauterine device called Mirena which releases 20 mcg of levonorgestrel, to reduce the thickening of the endometrium of the uterus, each day for up to 5 years.

Vaginal rings, comprising soft plastic rings of around 4 cm to 5 cm in diameter impregnated with a desired drug, are placed in the vagina around the cervix where they slowly release a drug into the bloodstream through the soft tissue of the cervix. Organon's Nuvaring releases oestrogen/progesterone.

Although the above provide long term local drug delivery to the pelvic region, for various reasons, they tend to suffer from low levels of patient compliance.

Typically creams and gels are considered by patients to be messy and unhygienic while vaginal rings can be uncomfortable, particularly during sexual intercourse, and may cause discharge. Intrauterine devices require inconvenient regular visits to the clinic for physician fitting and can cause severe discomfort such as stomach cramps due to the direct application of levonorgestrel to the endometrium of the uterus. In addition, such intrauterine devices may cause discharge, menstrual disturbance and fertility effects.

It is an aim of the present invention to provide means to deliver medicaments to the pelvic region which minimises the above difficulties.

According to the present invention there is provided an implantable medicament delivery device which is insertable into the myometrium or prostate comprising means capable of providing controlled delivery of a medicament over a period of time.

A medicament may be any pharmaceutical, neutraceutical, prophylactic or therapeutic agent wherein a therapeutic agent includes, but is not limited to, means for radiotherapy such as radioactive sources for example caesium, iridium, radioactive iodine, radioactive strontium or radioactive phosphorus.

The term "medicament" herein also includes energy sources which may be delivered to the myometrium by targeting the delivery device. Such energy sources include electromagnetic radiation, heating and cooling energies such as to selectively destroy tissues.

Preferably the medicament delivery device is an implant which can be insertable into the myometrium, or prostate and retainable therein for a defined period of time.

The retention of the implantable delivery device in the myometrium (in females) or prostate (in males) provides for direct and local delivery of a medicament to the pelvic region and organs thereof for example the bladder, peritoneum, bloodstream and in females the vulva, vagina, ovaries, fallopian tubes and uterus over a determined period of time.

Preferably the implantable delivery device is capable of being insertable in and retainable in the smooth muscle myometrial tissue of the cervix.

Insertion and retention of the implantable medicament delivery device in the myometrium of the cervix enables the implant to be checked and monitored by speculum examination or other visualisation or palpation following implantation.

Alternatively the implantable delivery device may be inserted in any suitable location in the myometrium, usually of the body of the uterus. The implant may be placed in the myometrium of the body of the uterus, or other positions not accessible by access via the vagina.

Preferably the implantable medicament delivery device comprises a body having an outer surface and opposing first and second ends said body comprising a medicament wherein the first end of the body is a semi-sharp point.

A semi-sharp point enables the tissue to be sufficiently disrupted to allow insertion of the implantable device, but causes minimal tissue damage.

In one preferred arrangement the body of the device is elongate and the second end of the body includes a head portion wherein the head portion is a lateral extension from the longitudinal axis of the elongate body.

Preferably the head portion is a substantially flat plate which extends in all radial directions from the second end of the body of the device.

The provision of a semi-sharp point at a first end of the delivery device is advantageous as it allows the device to be easily inserted into the smooth muscle of the myometrium or the tissue of the prostate.

Preferably the means capable of providing the controlled delivery of a medicament over a period of time is a pharmaceutically acceptable carrier such as at least one of a hydrogel, a silicone based material, elastomer, proteinaceous material, polyethylene glycol (PEG) material, polysaccharide or other carbohydrate material, microspheres, polymeric material or plastics material which may comprise, be contained by, or coated onto the device, or other means known to those skilled in the art.

Preferably the means capable of providing the controlled delivery of a medicament are present in the body of the device.

Alternatively, in those embodiments wherein there is a head, the means capable of providing the controlled delivery of a medicament may be present in the head of the device.

In particular embodiments the means are present in both the body and the head of the device.

In embodiments where the means capable of providing the controlled delivery of a medicament are provided in the body of the device, medicament delivery is substantially through the myometrium to the tissues and organs of the pelvic region.

In embodiments where the means capable of providing the controlled delivery of a medicament are provided in the head of the device, medicament delivery is substantially to the vaginal cavity and tissues and organs of the pelvic region.

Preferably the second end of the device includes retrieval means.

Retrieval means are advantageous as they allow the implant to be removed from the myometrium or prostate tissue after a determined period of time. Thus the delivery device can be easily removed from the body and does not require to be retained in the body forever. Removal of the implantable device provides a means of control over the length of time an active agent of a medicament is delivered.

The retrieval means can be any means which allow the removal of the implantable device from the myometrium or the prostate following a determined period of time.

In arrangements of the device which are insertable and retainable in the myometrium, preferably the retrieval means comprises an elongate flexible member, for example a thin length of cord, twine or fibre or string.

Preferably the elongate flexible member can be left outside the myometrium and soft tissue surrounding the uterus and/or vaginal cavity without causing irritation to a patient, nor affecting sexual intercourse. When it is desired to remove the implantable delivery device from the tissues in which the implant is inserted, for example the myometrium, the flexible member can be manipulated to pull the implant out of the tissue.

Preferably the second end of the device for example the head and/or retrieval means remain visible or palpable during examination by a physician when, in use, the delivery device is inserted into the myometrium or prostate.

This is advantageous as the location of the implantable delivery device can be easily monitored and checked by visual or physical inspection.

Preferably, the overall implantable device of the present invention is significantly smaller than the overall size of coils, IUD or vaginal rings. This is advantageous as there will be less discomfort to the person in which the drug delivery device is implanted and less likelihood of rejection of the implant by the body or responses such as inflammation.

Preferably the device has an axial length in the range 5 mm to 45 mm.

More preferably the device has an axial length in the range 10 mm to 45 mm.

Preferably the device has a diameter of from 0.5 mm to 4 mm.

Preferably the body has a large surface area to volume ratio. This has the advantage of providing maximal absorption of the drug into the surrounding tissues and/or smooth muscle.

The device of the present invention may be used to deliver a wide range of active agents for example, but not limited to, steroids, hormones such as a progestin, agents which promote a contraceptive effect, for example levonorgestrel or etonorgestrel, agents for treating disorders of the pelvis, for example, GnRH analogues, NSAIDs, COX-II inhibitors and aromatase inhibitors, vagina and organs and tissues thereof, cytotoxic agents for killing cancer cells or treating cancer, particularly cancer cells of the bladder, prostate or cervix or other pelvic malignancies and agents for the treatment of benign prostatic hypertrophy, impotence, erectile dysfunction and the like. Further, the device may be used to deliver agents for the treatment of an over active bladder, such drugs including anti-cholinergic drugs or calcium antagonists, Or agents for radiotherapy.

Preferably the medicament of the device is chosen from the group consisting of, but not limited to, anti-infectives, antimicrobials, antivirals, antibiotics, anti-allergenics, anti-inflammatories, anti-fungals, anti-cholinesterases, nutritional agents such as essential amino-acids, fats and vitamins, prebiotics, probiotics and acidifiers, cardiovascular agents, antihypertensive agents and chemotherapeutic agents.

Preferably the medicament is a therapy for oestrogen dependent proliferative disorders of the pelvis, for example endometriosis and/or fibroids and other pelvic disorders as would be known to those skilled in the art for example functional cysts and polycystic ovary syndrome.

Preferably said therapy for endometriosis includes progestins, GnRH agonists and antagonists, NSAIDs, COX-II inhibitors, combined oral contraceptives, Danazol, smooth muscle relaxants or aromatase inhibitors. The skilled person would also appreciate other similar therapies which could be used in relation to such disorders and the suitable dosage that would be required.

A drug delivered by the present invention may additionally or alternatively include a microbicide. A microbicide is any agent detrimental to, or destructive of, the life of microbes, viruses or bacterial organisms. Such a microbicide could be used to destroy organisms responsible for sexually transmitted diseases such as gonorrhoea, chlamydia, genital herpes, Human Immunodeficiency Virus, Human Papilloma Virus or bacterial vaginosis.

The concentration and the time period over which the above active agents and those described below should be provided will be as determined by those skilled in the art. Those skilled in the art can determine these parameters, which depend on for example the potency (the amount required to effect the desired change), toxicity and in vivo diffusion of the active agent using standard procedures.

Preferably, in use, the cumulative release of therapeutic agent is in an amount selected from 5%, 10%, 15%, 20%, 25%, 30%, 40%, 50%, 60%, 70%, 80%, 90%, 95%, 99% and 100% relative to the total amount of medicament in the device after implantation for a period of 1 week, 2 weeks, 1 month, 2 months, 3 months, 4 months, 6 months, 1 year, 2 years, 3 years, 4 years or 5 years.

According to a second aspect of the present invention there is provided a kit for implanting a device of the first aspect of the invention comprising a device according to the first aspect of the invention and an insertion tool, said tool comprising an elongate shaft, said shaft having handle means at a first end thereof and device mounting means at a second opposite end wherein the medicament delivery device of the first aspect of the invention is mountable on the insertion tool.

According to a third aspect of the present invention there is provided a method of providing a medicament to a female mammal comprising the step of inserting a device according to a first aspect of the invention into the myometrium.

The implantable delivery device is capable of being inserted into the smooth muscle myometrial tissue of the cervix via the vagina, into the myometrium of the uterine body through serosa surrounding the myometrium during open or laparoscopic surgery or into the myometrium through the endometrial cavity.

Preferably the method of the third aspect of the invention comprises the steps of
a) providing the implantable medicament delivery device of the first aspect of the invention,
b) introducing the medicament delivery device into the body via the vagina,
c) penetrating the myometrium with the medicament delivery device, and
d) inserting the medicament delivery device into the myometrium.

Preferably the method further comprises the step of mounting the implantable medicament delivery device on an insertion tool.

Particular embodiments of the medicament delivery device are implantable in the prostate. The prostate is a gland in males which surrounds the urethra below the bladder.

Preferably the implant is insertable into the prostate by a transrectal route. Alternatively the implant can be inserted into the prostate by a trans-perineal route.

Preferably the medicament delivery device is insertable into the prostate using ultrasound. Provision of an implantable medicament delivery device in the prostate has the advantage that drugs can be delivered to the tissue of the prostate, tissue surrounding the prostate, and the bloodstream. Further, delivery of drugs directly to the prostate means the drugs are not subjected to liver metabolism as would be the case for drugs provided orally.

Preferably the prostate implantable medicament delivery device provides for the cumulative release of a therapeutic agent in an amount selected from 5%, 10%, 15%, 20%, 25%, 30%, 40%, 500, 60%, 70%, 80%, 90%, 95%, 99% and 100% relative to the total amount of medicament in the device after implantation for a period of 1 week, 2 weeks, 1 month, 2 months, 3 months, 4 months, 6 months, 1 year, 2 years, 3 years, 4 years or 5 years.

According to a fourth aspect of the present invention there is provided the use of a delivery device according to the first aspect of the invention to provide long term local delivery, for example 3 months to 5 years, of medicaments to the pelvic region and organs thereof, for example to the bladder, peritoneum, vulva, vagina, ovaries and uterus.

In one preferred embodiment of the fourth aspect of the invention a device according to the first aspect of the present invention is used to deliver medicament(s) to treat gynaecological conditions, for example endometriosis, fibroids, cervical cancer or overactive bladder.

In a second preferred embodiment of the fourth aspect of the invention a device according to the first aspect of the present invention is used to treat male conditions for example benign prostatic hypertrophy, impotence, erectile dysfunction and the like.

The medicament delivery device and method of the present invention promote smooth, controlled release of drugs to the pelvic region, which allows absorption of drugs without subjecting drugs to liver metabolism.

Embodiments of the present invention will now be described by way of example only with reference to the accompanying drawings, in which.

Figure 1:
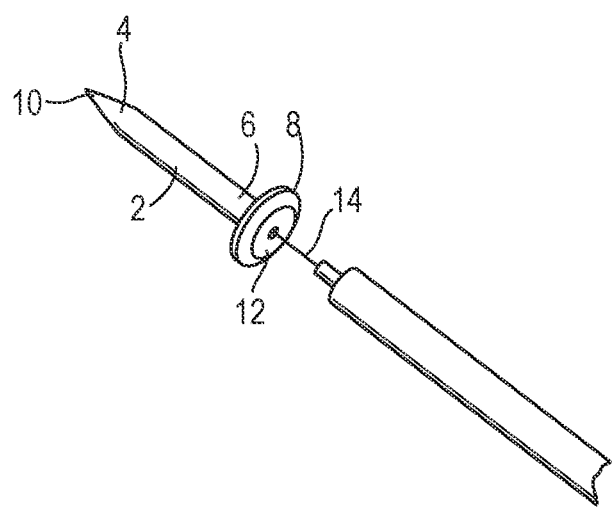
FIG. 1 is an illustration of an implantable medicament delivery device according to the invention for delivery of medicament to the tissues of the myometrium and pelvic region.

Referring to FIG. 1, in one embodiment, the implantable medicament delivery device comprises an elongate cylindrical body 2 with a first end 4 and a second end 6. In this embodiment head portion 8 extends laterally from the second end 6 of the body 2 such that a flange is provided around the circumference of the body 2 at the second end. A semi-sharp point 10 is provided at the first end 4 of the body 2. In the embodiment shown the head portion 8 is a substantially flat plate which includes a depression 12. When, in use, the body of the device is implanted in the tissues of the myometrium, the head portion 8 minimises the likelihood of the tissue of the implant being pushed too far into the tissue during insertion of the implant or the myometrium tissue growing over the implant. It also provides means by which the position of the implant can be checked by visual or physical means.

In the embodiment described which is insertable into the myometrium, retrieval means 14 are provided by a cord. The cord extends substantially from the centre point of the depression 12 in the head portion 8. In use, the cord extends from the second end of the implant and allows the device to be removed from the tissue after suitable delivery of the medicament or if the patient requests removal. The device is typically retained in the body for at least a day, a few weeks, months or up to 5 years. It may be removed at any point during this period. In embodiments wherein the device is comprised of biodegradable material the device may not need to be removed at a later time point and thus will not require a head portion or retrieval means.

In this embodiment the means capable of providing controlled delivery of the medicament is located in or on the elongate body 2 of the device. Delivery of the medicament is substantially through the myometrium and into pelvic organs and tissues. This embodiment of the device is particularly advantageous for the delivery of medicament for the treatment of endometriosis and or fibroids.

Figure 2:
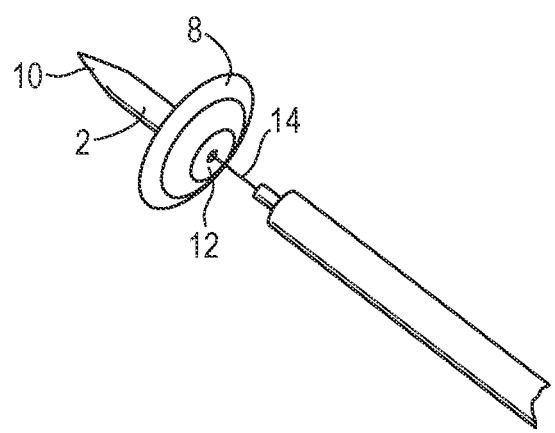
FIG. 2 is an illustration of an implantable medicament delivery device according to the invention for delivery of medicament to the tissues of the vaginal cavity and pelvic region.

FIG. 2 shows an embodiment of the present in invention wherein the elongate body 2 may be shorter in length, approximately 5 mm to 20 mm in length and in which the head portion 8 is larger typically around 12 mm in width. In such an embodiment the means capable of providing controlled delivery of a medicament over a period of time is located in or on the head portion.

In use, the body 2 is inserted in the tissues of the myometrium and the head portion remains in the vaginal cavity. This embodiment of the device substantially delivers medicament to the vaginal cavity, mucosa thereof and pelvic tissues, such an embodiment is particularly advantageous for delivery of medicaments suitable for treating bacterial vaginosis.

Figure 3:
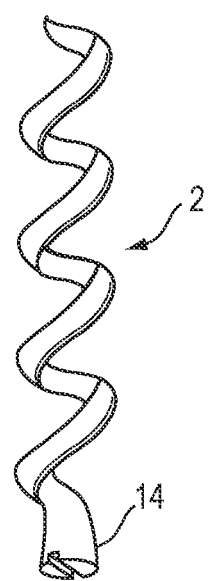
FIGS. 3, 4, 5 and 6 are illustrations of embodiments of the medicament delivery device according to the invention.
Figure 4:
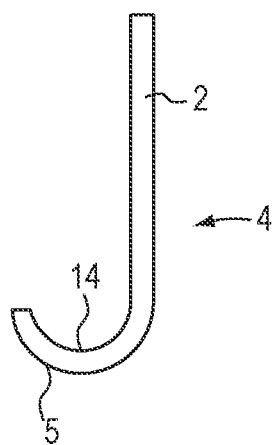
Figure 5:
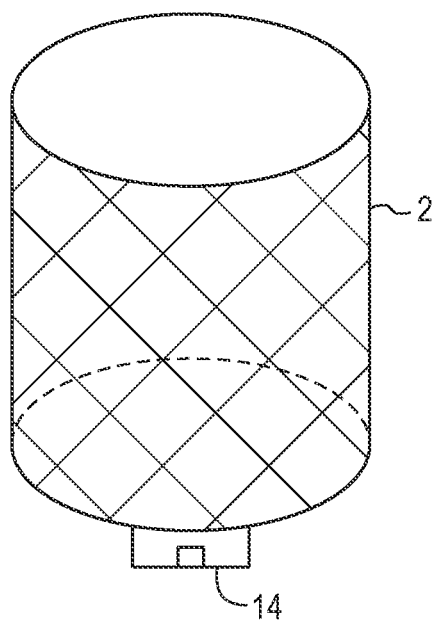

Alternative embodiments of the implantable device are illustrated by FIGS. 3 to 6. In these embodiments the body of the implant may be spiral or corkscrew shaped (FIG. 3), generally J or U shaped such that the second end of the implant forms a loop or hook (FIGS. 4 and 6) or an elongate mesh cylinder (FIG. 5). As shown in FIG. 4 a semi-sharp point may not be required at the first end of the body 4 to allow insertion into the tissues.

The body may be any suitable shape which allows the implant to be inserted into the myometrium or prostate. Indeed the cross section of the body can be of any preferred shape, which allows insertion of the implant into the myometrium or prostate, or that influences the drug delivery characteristics of the implantable delivery device. For example the body of the device may be cross-shaped to increase the surface area of the delivery device exposed to the surrounding tissue. Further, the body may be formed by a mesh or other method to increase the surface area of the implant in contact with the myometrial or prostate tissue. The amount of surface area of the implant in contact with surrounding tissue or muscle can influence the drug delivery characteristics of the implant.

Figure 6:
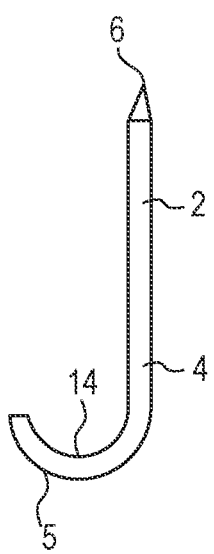

As shown in FIGS. 4 and 6 the retrieval means may comprise a hook at the second end of the implantable device wherein the second end of the body 2 is bent toward the first end to provide a hook. In this embodiment the retrieval means restricts the body 2 from becoming buried in the soft tissue enabling retrieval of the implant from soft tissue and the smooth muscle of the myometrium or the prostate. In addition, the hook provides means by which the location of the implant can be checked by a physician by visual or physical means.

Alternatively, as shown in FIG. 3, the retrieval means can be a slot capable of accepting a screwdriver or other means for rotating the implantable delivery device in the tissue to insert or remove the device from the tissue.

In the embodiment illustrated by FIG. 1 the body 2 comprises the medicament delivery means. In particular embodiments, not shown in FIG. 1, a length of the body 2 between the point 4 and retrieval means 14 may have a reduced diameter relative to the diameter of the body 2 at the first 4 and second ends 6. In such embodiments the drug delivery means may comprise a cylinder of material formed around the reduced diameter portion of the body 2. The medicament delivery means can be any suitable pharmaceutically acceptable carrier for example, a hydrogel carrying the active agent to be delivered by the medicament delivery device. In another example, the delivery means is a silicone based material, elastomer, proteinaceous material, polyethylene glycol (PEG) material, polysaccharide or carbohydrate material, microspheres, polymeric material or plastics material which may comprise, be contained by, or coated onto the device. The above drug delivery devices may also comprise, be contained by, or coat the head 8 of the device. This allows, as discussed in relation to the embodiment illustrated in FIG. 2, for delivery of medicament to the vaginal cavity.

In a preferred embodiment, the body of the implant which may be porous, non-porous or microporous, can be dipped into a solution of the selected drug delivery medium containing a solution or slurry of drug, such that a thin layer of drug and drug delivery medium is coated onto the body of the implant and bonds securely in the dry state to the body of the implant via a mechanical or adhesive hold.

Alternatively, the medicament can be impregnated, or absorbed by or into the device and allow the medicament to be released over time. As a further alternative the medicament may be applied to the device using any suitable means that allow the medicament to be attached or bonded to the device and which allow the medicament to be available for absorption/release into the surrounding tissues, for example the myometrium or vaginal cavity.

The drug delivery medium may be capable of slowly releasing the active agent of the medicament into the myometrium, vaginal cavity or the prostate, and thus providing drugs to the pelvic region and organs thereof the surrounding soft tissues and blood vessels.

Hydrogel releases drug by diffusion or via microcracks in the hydrogel. An alternative biodegradable hydrogel system releases drug via an erosion or degradation mechanism. Varying release rates of drugs can be achieved, as can continuous dosing with small levels of drugs, and flexibility of drug release may depend on different drugs being utilised Depending of the release characteristics of the hydrogel and the chemical composition of the active agent; release of the active agent will typically occur up to 5 years from implantation of the delivery device.

The medicament delivery device may be formed by any biocompatible material, for example the medicament delivery device can be formed from plastics or biocompatible metals. Suitable materials include, but are not limited to, high density polyethylene (HDPE), ultra high molecular weight polyethylene (UHMWPE), polypropylene (PP), polyvinyl chloride (PVC), polymethylmethacrylate (PMMA), polyethyleneterephthalate (PET), polytetra-fluoroethylene (PTFE), polycarbonate (PC), styrene-butadine-styrene (SBS), stainless steel (361/316L/317), nickel free stainless steel, cobalt chrome alloy (CoCrMo), titanium (specifically Ti6Al4V) and Liquid Metal.

In one particular embodiment of the delivery device, the delivery device is formed from the medium carrying the drug. In this example, if the medium carrying the drug is absorbable, the complete delivery device may be absorbed by the body over the period of time that the drug is administered.

Wherein the implant itself is the medium by which the drug to be administered is carried it can be envisaged that an insertion device for example a trocar containing the implant may be used to deliver the implant. In this embodiment the delivery device may be pushed out of or injected from the trocar into the myometrium 44. The use of an implant comprising the medium in which the drug to be administrated is included, would allow insertion of the implant into the myometrium 44 and delivery of the drug to be limited to a shorter time scale for example 1 day, 3 months to 12 months. The implant would not require to be removed at a later date as it may degrade over time and be absorbed by the body.

The drug may be delivered to the myometrium 44 and be absorbed within a few minutes, hours, days or weeks depending on the medium. It can be appreciated that where the implant comprises the drug delivery medium, removal of the implant is not required. An absorbable implant therefore does not require retrieval means.

The uterine myometrium has few or no somatic pain fibres and thus insertion, provision and withdrawal of the implant in the myometrium will cause minimal pain and discomfort to the patient.

A device of the present invention capable of being implanted into the myometrium tissue is advantageous over subcutaneous delivery devices previously known in the art, such as Norplant® which are inserted under the skin which has somatic sensory (pain) nerves.

As there is little tissue or muscle movement in the myometrium compared with for example the tissues of the arm or the leg and the myometrium does not comprise as many layers or planes of tissue as in the arm or leg, there is little likelihood of the implant moving to a different location following insertion.

Figure 7:
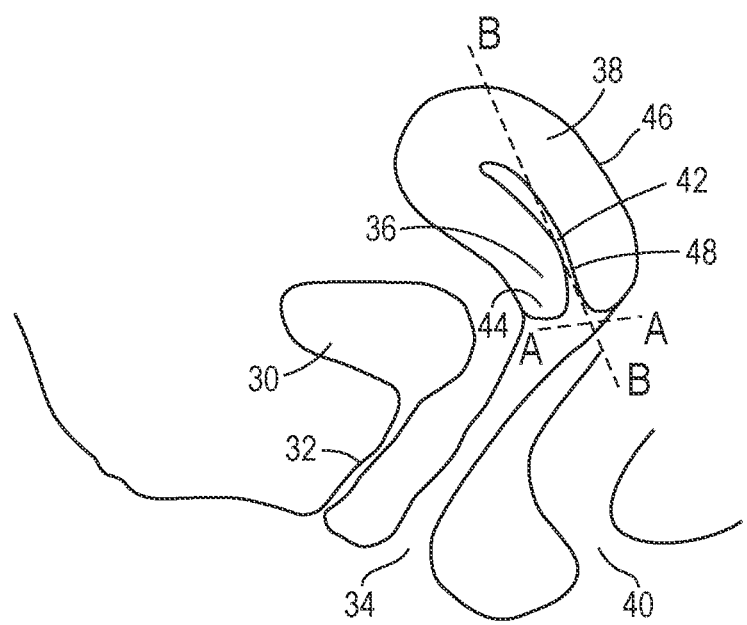
FIG. 7 is a saggital illustration of the female pelvic region of a medicament delivery device of FIG. 1 in use.
Figure 8:
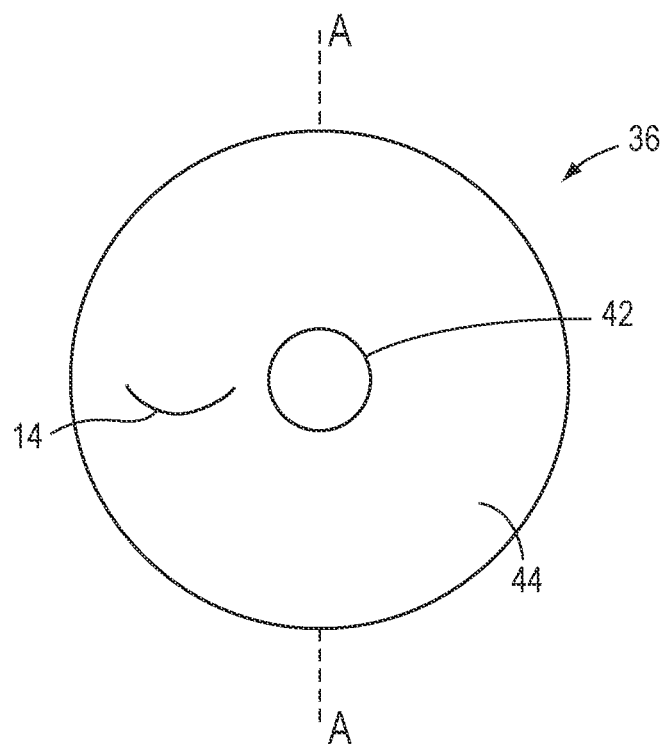
FIG. 8 is an end view of the illustration in FIG. 4 along the line A-A illustrating the placement of the device.
Figure 9:
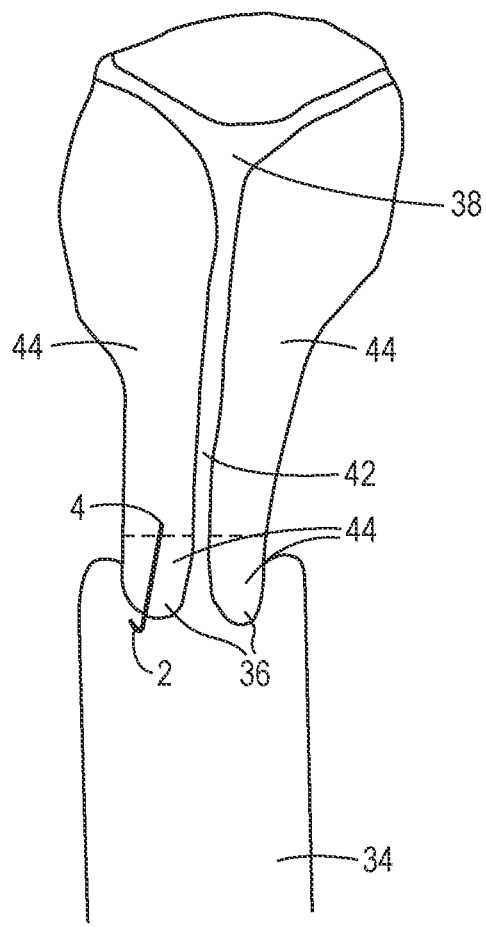
FIG. 9 is a coronal view of the illustration in FIG. 4 along line B-B.

As shown in FIG. 7, the female human genital area comprises a bladder 30, urethra 32, vaginal cavity 34, cervix 36, uterus 38 and anus 40. In particular, the cervix 36, at a position between the vaginal cavity 34 and uterus 38, comprises the cervical canal 42 leading from the vaginal cavity 34 into the uterus 38 and surrounding smooth muscle known as the myometrium 44. The myometrium is defined by the serosa 46 (an epithelial layer of cells) and the endometrium 48. An end view of the cervix along line A-A is shown in FIG. 8.

In use, an embodiment of the implant can be inserted into the myometrium via the vagina and then through the cervix or alternatively may be inserted into the myometrium during open or laparoscopic surgery.

The myometrium of the cervix is in a convenient location, at the top of the vaginal cavity, for insertion and removal of the implant via vaginal access. Further insertion of the device by this route has the advantage that the implant can be suitably located using a speculum in an outpatient setting. The insertion of the implant in the myometrium would be similar in both the time taken and the discomfort to the patient as the taking of a smear.

Insertion of the implantable medicament delivery device during open or laparoscopic surgery has the advantage of allowing the implant to be placed at any suitable location in the myometrium, usually in the body of the uterus. The implant may thus be placed in the myometrium of the body of the uterus, or other positions which would not be accessible by access via the vagina.

Location of the implant within the smooth muscle myometrial tissue of the cervix and uterus provides a novel means of drug delivery to the pelvic region and organs thereof for example to the bladder, peritoneum, vulva, vagina, ovaries and uterus. Local delivery of active agents of a medicament via insertion of the implant in the uterine myometrium promotes rapid, efficient absorption of the active agent directly into these organs the surrounding tissue and then the bloodstream. Further, delivery of medicaments in this way avoids the first pass liver effect.

The active insertion of the implantable delivery device into the smooth muscle of the cervix of the uterine body means that the present invention differs from an IUD or a vaginal ring as an IUD is located in the cavity of the uterus (endometrium) and vaginal rings are placed at the top of the vagina around the cervix.

While inserted in the myometrium the device will not be felt by the patient. As previously discussed, this provides a further advantage of the present invention over intrauterine devices and vaginal rings. Furthermore, the device of the present invention will not cause menstrual or fertility disturbances and will be acceptable to women of a range of religious faiths.

Moreover, drug delivery by means placed around tissues or in cavities such as vaginal rings and intrauterine devices can suffer from decreased absorption as the active agents have to pass through epithelial layers overlying the surrounding tissues before they enter the tissue. For example, drugs released from a vaginal ring must pass through the vaginal epithelium before being absorbed into the vaginal wall and passing into the blood stream.

Locating medicament delivery means and delivery of the medicament in the myometrium minimises the risk of poor absorption as the active agents are not required to pass through epithelium. Medicament absorption is facilitated by high local blood flow.

In particular embodiments locating medicament delivery means in the myometrium and delivery of the medicament into the vaginal cavity enables delivery to the epithelium lining the vagina and the local tissues thereof.

Therefore drug delivery directly into the myometrium or vagina will likely require smaller amounts of a drug to achieve significant clinical affect, substantially reducing the risk of side effects.

In specific embodiments of the medicament delivery devices, suitable for delivery of drugs to the tissues of the myometrium, for example FIG. 1, the body 2 of the medicament delivery device typically has a diameter of 2 mm and a length of 20 mm. These diameters and lengths are, of course, for guidance only and other suitable dimensions will be apparent to those skilled in the art. For example depending of the amount of drug to be delivered the length of the body may be 20 mm or 30 mm.

FIG. 2 shows an embodiment of the device for delivery of drugs to the vaginal cavity. In this embodiment, the body is preferably around 5 to 10 mm in length and the head is around 8 to 15 mm in width.

The implant may have any structure suitable for insertion and retention in the smooth muscle of the myometrium or the tissue of the prostate. For example the implant may comprise barbed portions or surface patterns to promote retention of the implant in the myometrium or prostate. This may be advantageous if movement of the tissue in which the implant is inserted is likely to cause the implant to work loose and move from its intended position.

To aid insertion of the medicament delivery device into the myometrium by a vaginal route an insertion tool may be used.

Figure 10:
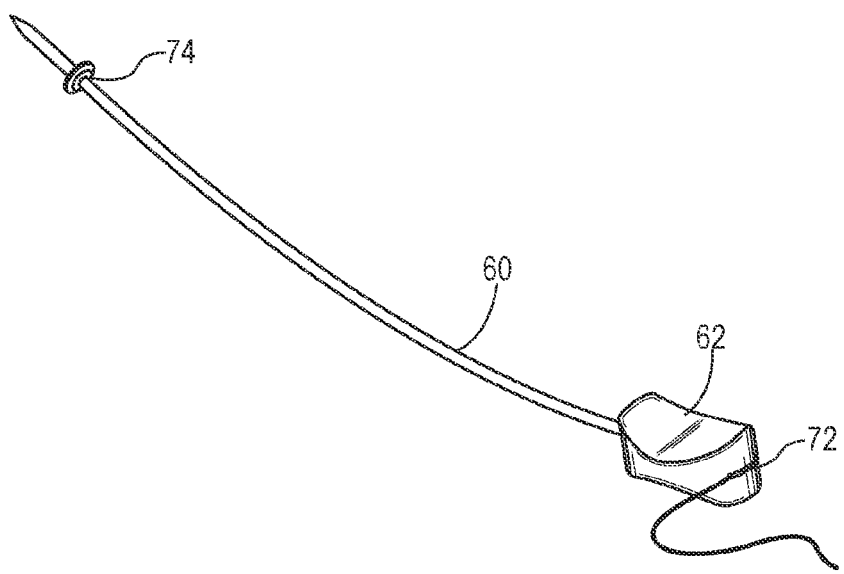
FIG. 10 shows an illustration of the embodiment of a medicament delivery device as shown in FIG. 1 mounted on an insertion tool.
Figure 11:
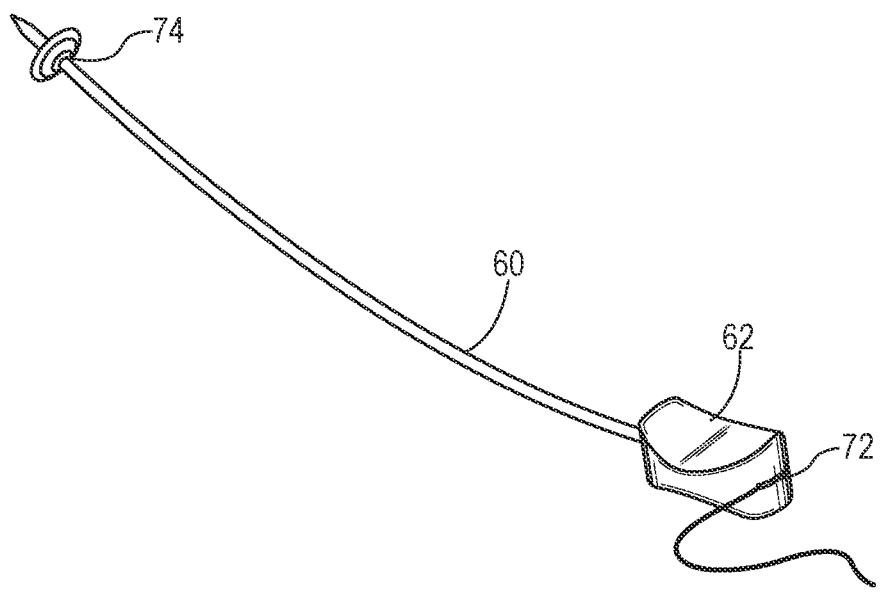
FIG. 11 shows an illustration of the embodiment of a medicament delivery device as shown in FIG. 2 mounted on an insertion tool.
Figure 13:
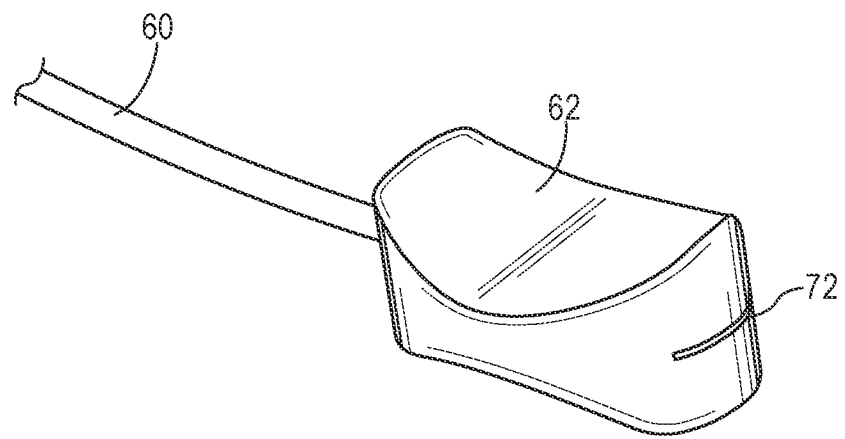
FIG. 13 shows an embodiment of a handle means of an insertion tool.
Figure 14:
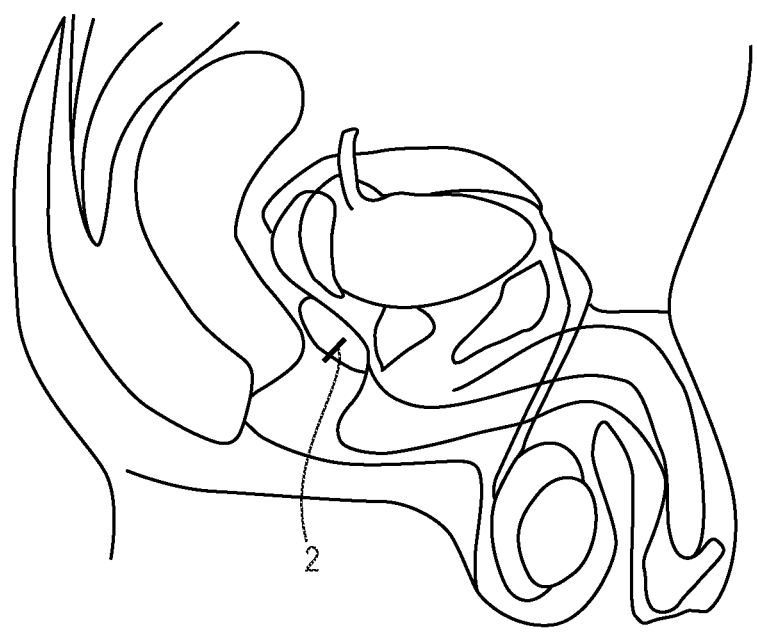
FIG. 14 is an illustration of an embodiment of an implant of the present invention inserted in the prostate.

An embodiment of an insertion tool is shown in FIGS. 10 and 11 with the implantable devices illustrated by FIGS. 1 and 2 respectively mounted thereon. In the embodiment shown, the insertion tool comprises a curved stainless steel shaft 60 of approximately 20 to 25 cm in length and around 2 mm in diameter. A handle element 62 of around 2 to 4 cm may be provided on the shaft. A particular embodiment of a handle element is illustrated in FIG. 13.

Figure 12:
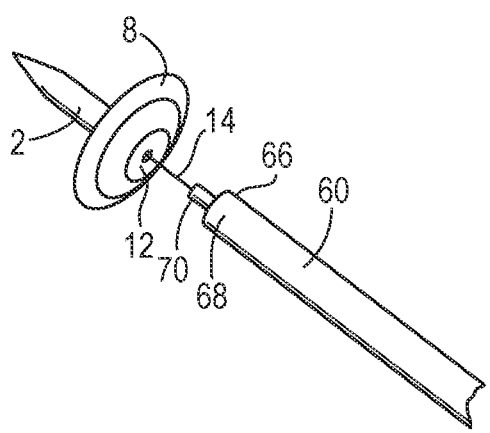
FIG. 12 shows an illustration of an embodiment of device mounting means wherein the mounting means are formed by a stepped protrusion on the insertion tool capable of cooperating with a depression provided on the delivery device.

A first end of the shaft is provided with device mounting means 74 and a second end is provided with handle means 62. In the example shown the device mounting means, illustrated more clearly in FIG. 12, comprises a stepped protrusion 66 which provides a surface 68 against which the second end of the implantable device can abut. In particular, as shown in FIG. 12 a protruding portion 70 of the device mounting means is received by the depression 12 provided on the head portion 8 of the implantable device. The cord 14 of the implantable device is pulled along the length of the shaft 60 and is releasably fixable in a notch 72 provided in the handle means 62 of the insertion tool. The fixing of the cord 14 in the notch 72 aids the mounting of the device on the shaft of the insertion tool.

The device is mounted on the first end of the insertion tool and then the device is introduced into the body via the vagina. Using the insertion tool the device is advanced into the vagina 34 towards the cervix 36 and inserted into the myometrium 44. The point 4 of the implant facilitates the easy insertion into the smooth muscle of the myometrium 44.

The device is inserted into the myometrium until only the head portion of the device or retrieval means remain outside.

After a determined period of time, the implant can be removed from the myometrium. Removal may be due to the implant reaching the end of its useful life, i.e. the drug has been administered for the intended length of time or the patient requesting removal of the implant. The implantable delivery device can be removed by pulling on the retrieval means 14, for example a cord or hook to withdraw the implant from the myometrium 44. Again, this is a straightforward procedure without routine need for local anaesthetic.

The delivery device is typically removed from the tissue after it has released a therapeutic agent in an amount selected from 5%, 10%, 15%, 20%, 25%, 30%, 40%, 50%, 60%, 70%, 80%, 90%, 95%, 99% and 100% relative to the total amount of medicament in the device after implantation for a period of 1 week, 2 weeks, 1 month, 2 months, 3 months, 4 months, 6 months, 1 year, 2 years, 3 years, 4 years or 5 years.

Alternative insertion tools may be used to insert the device.

For example if the implant has a blunt first end 4, as illustrated in FIG. 4, an insertion tool with a semi-sharp point may be used to penetrate the myometrium or prostate tissue and enable insertion of the implant.

This may be advantageous, as the implant which is retained in the tissue does not then require to have a semi-sharp portion.

In further embodiments of the insertion tool, instead of or in addition to device mounting means, the insertion tool may comprise means for releasably containing the implant within the tool. This embodiment of the insertion tool is driven into the myometrium, the implantable device is released into the myometrium and the tool is then withdrawn leaving the implant in place. For example, the insertion tool may comprise a collar for releasably retaining the medicament delivery device.

During insertion, use and removal the implantable device may be manipulated using any suitable surgical tool, such as forceps or the like.

As discussed above, the implantable medicament delivery device can be provided with medicament for release into the surrounding tissues in a number of ways.

Where the medium carrying the active agent of the medicament is provided by the body of the delivery device, the agent is released from the medium and passes through drug delivery means present in the delivery device to enter the surrounding tissue, for example the myometrial tissues. Drug delivery means may be provided along the entire length, at least part of the body, the head, or the body and head of the implantable device.

When inserted in the myometrium the body of the medicament delivery device is surrounded by smooth muscle and soft tissue. As smooth muscle of the cervix is highly vascularised, drug delivery to these tissues show good pharmacokinetics.

These drugs are able to pass through the highly vascularised tissues of the myometrium and target the pelvic region and organs thereof, for example, the bladder, peritoneum, and in females the vulva, vagina, ovaries and uterus. The drugs may further enter the bloodstream without being subjected to first pass liver metabolism.

Alternatively, drug delivery means may be provided at the head portion at the second end of the delivery device. When, in use, the implant is inserted into myometrial tissue, the head portion protrudes from the myometrial tissue into the vagina. In this particular embodiment, the implant provides a means of targeting drug delivery to the tissues of the vagina.

The implantable delivery device may be retained in the myometrium or the prostate and drug delivered over a period of at least, 1 day, 1 to 3 months, 1 to 6 months, 1 to 12 months, 1 to 2 years, 1 to 3 years or 1 to 5 years.

The implant of the present invention may be used to deliver a wide range of drugs. In particular, the implant can be used to deliver drugs which cannot be delivered orally.

Examples of conditions which can be treated using the drug delivery device will now be provided.

Endometriosis

Endometriosis is a painful condition caused by the endometrium (cells lining the uterus) migrating to other parts of the body. This can cause functional and hormonally responsive endometrial lesions. Typically lesions are found on the uterine muscles, ovary, peritoneum and intestine. Symptoms of endometriosis include excessive bleeding, dysmenorrhea, pelvic pain and infertility (up to 60% of women suffering from endometriosis become infertile).

Fibroids

Fibroids or myoma are benign encapsulated tumours of the smooth muscle and/or fibrous tissue elements of the uterine myometrium. They are usually asymptomatic, but may give rise to menstrual and/or fertility problems.

At present, an oral treatment (Danazol) is one of the most effective drugs to treat endometriosis, but the androgenic side effects of this drug limits treatment to 6 months. Endometriosis can also be treated using subcutaneous depot injections or nasal sprays of GnRH analogues. However, these treatments also have unpleasant side effects such as bone density loss, hot flushes and nausea.

The present implantable medicament delivery device provides pharmacokinetic advantages over the above for the treatment of endometriosis and fibroids. In particular the present delivery system provides long term delivery of a drug locally to the pelvic region, without the disadvantage of current local delivery systems such as vaginal rings or intrauterine devices.

A number of active agents may be provided using the device of the present invention for treatment of endometriosis.

Progestin

Progestins have advantages over Gonadotrophin Releasing Hormone (GnRH) Agonists in that they are cheaper with an improved side effect profile. In addition, Progestin therapy is most effective in controlling the symptoms associated with endometriosis, more specifically dysmenorrhea.

Progestin refers to synthetic progestogens wherein Progestogen is a generic term for all substances with progesterone like activity. Progesterone refers to the natural progesterone molecule.

There are two main groups of progestogen, progesterone and its analogues (dydrogesterone, gestrinone and medroxyprogesterone) and testosterone analogues (norethisterone and norgestrel). The newer progestogens (desogestrel, megestrol, norelgestromin, norgestimate, etonogestrol, ethynodiol or ethynodiol and gestodene) are all derivatives of norgestrel; levonorgestrel is the active isomer of norgestrel and has twice its potency. Progesterone and its analogues are less androgenic than the testosterone derivatives. Testosterone analogues are the norethindrone family (estranes)—including norethindrone, norethindrone acetate, ethynodiol diacetate, lynestrenol, and norethisterone acetate; and the levonorgestrel family (gonanes)—including levonorgestrel, norgestrel, desogestrel, norgestimate, gestodene, megestrol, norelgestromin, and etonogestrol.

Common progestins include medroxyprogesterone and levonorgestrel.

Non Steroidal Anti Inflammatory Drugs (NSAIDS)

Non Steroidal Anti Inflammatory Drug (NSAIDs) have good efficacy, low cost and comparatively mild side effect profile, and offer immediate pain management. They are most effective in controlling the symptoms associated with endometriosis. Common NSAID's include mefenamic acid, diclofenac or piroxicam.

GnICH Analogues

The main therapy shown to improve the severity of endometriosis is the gonadotrophin releasing hormone (GnRH) agonists.

However, this class suffers two main drawbacks, these being cost and severe side effects profile primarily bone density loss associated with inducing a temporary chemical menopause. Common GnRH agonists include leuprolide, goserelin and nafarelin.

In addition to the above sole therapies the device of the present invention can also be used to deliver a number of combination therapies. For example, Progestin/NSAID, Progestin/GnRH analogues, GnRH/NSAID or, GnRH add back therapy (tibolone)

GnRH with Add Back Therapy

Add-back therapy in conjunction with a GnRH agonist does not eradicate bone loss, however it does reduce the rate of bone demineralization and hence, enable longer use of GnRH agonists. The progestin tibolone is of particular interest for use as add back therapy, particularly for osteoporosis prophylaxis.

Owing to the poor solubility of all proposed drugs in water, a hydrogel (flooded with water, thus low driving farce only required to release drugs) is ideally used as the drug carrier on the implant. The porous but permeable active drug/carrier can be coated onto the body of the implant via mechanical/adhesive hold. In such an embodiment a microporous implant may be necessary. This exterior coating of hydrogel/active drug may be biodegradable and should be a highly concentrated but thin layer (high drug reservoir/low distance to travel) to obtain maximum rate of drug release via an erosion mechanism.

The amount of drug required to elicit effect can be determined by those skilled in the art, using conventional means. However, estimates of the amount of a drug which may be provided based on preliminary results which should not be considered limiting in any way on the device of the present invention are given below by way of example only.

Levonorgestrel

Currently, oral daily doses for levonorgestrel are 60 mcg. Using vaginal delivery analogy of 10% drug required compared to oral doses, daily myometrial doses would be 6 mcg for levonorgestrel A mare feasible daily dose to enable drug delivery via a hydrogel would likely be 20 mcg for levonorgestrel (33%; of oral dose)

Assuming 50% w/w of drug to hydrogel, the total weight of the drug/carrier layer could be in the range of 3 to 15 mg.

The body of the implant could accommodate 3, 6 or 12 month or longer doses.

Leuprolide

Currently, the daily dose for leuprolide is 125 mcg (intramuscular). Typical daily myometrial doses could be around 62 mcg for leuprolide (50% of intramuscular dose)

However in the absence of clinical data, it is impossible to estimate the clinical effectiveness of such doses of leuprolide.

Assuming 50% w/w of drug to hydrogel, the total weight of the drug/carrier layer would be in the range of 10 m to 45 mg.

The body of the implant could accommodate 3, 6 or 12 month or longer doses.

Piroxicam

Currently, oral daily doses for piroxicam are 10 to 40 mg. Using vaginal delivery analogy of 10% drug required compared to oral doses, a daily myometrial doses could be 3 mg for piroxicam. A more feasible daily dose to enable drug delivery via a hydrogel could be 300 mcg for piroxicam (1% of oral dose). However in the absence of clinical data, it is impossible to estimate the clinical effectiveness of such low doses of piroxicam.

Assuming 50% w/w of drug to hydrogel, the total weight of the drug/carrier layer would be around 50 to 220 mg.

The body of the implant could accommodate 3, 6, or 12 month or longer doses.

Levonorgestrel/Piroxicam

Currently, oral daily doses for levonorgestrel are 60 mcg, and piroxicam 10-40 mg. Using vaginal delivery analogy of 10% drug required compared to oral doses, daily myometrial doses could be 3 mg for piroxicam 6 mcg for levonorgestrel. A more feasible daily dose to enable drug delivery via a hydrogel (levonorgestrel dose as per Mirena coil dose) would be 300 mcg for piroxicam (1% of oral dose), 20 mcg for levonorgestrel (33% of oral dose). However in the absence of clinical data, it is impossible to estimate the clinical effectiveness of such low doses of piroxicam.

Assuming 50% w/w of drug to hydrogel, the total weight of the drug/carrier layer would be in the range of around 55 mg to 230 mg.

The body of the implant could accommodate 3, 6, 12 month or longer doses.

Levonorgestrel/Leuprolide

Currently, daily doses for levonorgestrel are 60 mcg (oral), and leuprolide 125 mcg (intramuscular). Using vaginal delivery analogy of 10% drug required compared to oral doses, daily myometrial doses could be 62.5 mcg for leuprolide and 6 mcg for levonorgestrel. A more feasible daily dose to enable drug delivery via a hydrogel would be 62.5 mcg for leuprolide (50 W of intramuscular dose) and 20 mcg for levonorgestrel (33% of oral dose). However in the absence of clinical data, it is impossible to estimate the clinical effectiveness of such low doses of leuprolide.

Assuming 50% w/w of drug to hydrogel, the total weight of the drug/carrier layer could be in the range of around 14 mg to 60 mg.

The body of the implant could accommodate 3, 6, 12 month or longer doses.

Leuprolide/Tibolone

Currently, daily doses for leuprolide are 125 mcg (intramuscular), and tibolone 2.5 mg (oral). Using vaginal delivery analogy of 10% drug required compared to oral doses daily myometrial doses could be 62.5 mcg for leuprolide (50% of intramuscular dose) and 250 mcg for tibolone. However in the absence of clinical data, it is impossible to estimate the clinical effectiveness of such doses of leuprolide.

Assuming 50% w/w of drug to hydrogel, the total weight of the drug/carrier layer would be in the range of around 55 mg to 225 mg.

The body of the implant could accommodate 3, 6 or 12 month or longer doses.

Leuprolide/Piroxicam

Currently, daily doses for leuprolide are 125 mcg (intramuscular), and piroxicam 10-40 mg (oral). Using vaginal delivery analogy of 10% drug required compared to oral doses daily myometrial doses could be 62.5 mcg for leuprolide and 3 mg for piroxicam.

A more feasible daily dose to enable drug delivery via a hydrogel could be 62.5 mcg for leuprolide (50% of intramuscular dose) and 300 mcg for piroxicam (1% of oral dose). However in the absence of clinical data, it is impossible to estimate the clinical effectiveness of such doses of piroxicam and leuprolide.

Assuming 50% w/w of drug to hydrogel, the total weight of the drug/carrier layer would be in the range of around 65 mg to 261 mg respectively.

The body of the implant could accommodate 3, 6 or 12 month or longer doses.

Bacterial Vaginosis

Bacterial vaginosis, an abnormal colonisation of the vagina which may lead to vaginitis, is an inflammation which occurs in the vagina. It includes several strains of organism that cause bacterial vaginosis, yeast infections and trichomoniasis. Bacterial vaginosis occurs mostly during the reproductive years although women of all ages are susceptible. Typically infection affects the vagina, urethra, bladder and skin in the genital area.

Primary causes of bacterial vaginosis include an overgrowth of anaerobic bacteria and the Gardnerella organism. Although the healthy vagina includes a small amount of these bacteria and organisms, when the vaginal balance is disrupted by the overgrowth of these bacteria, another protective aerobic bacterium (lactobacilli) is unable to adequately perform its normal function. Lactobacilli normally provides a natural disinfectant (similar to hydrogen peroxide) which helps maintain the healthy and normal balance of microorganisms in the vagina. The vaginal anaerobic to aerobic bacteria ratio is 1000 to 1, normal vaginal flora is 5 to 1 ratio. During vaginosis a change in pH of vaginal fluid also occurs.

Bacterial Vaginosis can cause a range of symptoms such as discharge. In addition, the change in pH of the vaginal fluid to more than 4.5 can also cause odour and some itching.

The medicament delivery device of the present invention may be used to deliver medicaments to restore normal vaginal bacteria by inhibiting anaerobic bacteria, but not the normal vaginal lactobacilli, in order to eliminate symptoms of discharge and odour.

In particular embodiments, one of which is illustrated in FIG. 2 and discussed above, the medicament delivery device has a body portion for insertion into the myometrium and a head portion which extends into the vaginal cavity. The body portion is preferably around 5 mm to 20 mm in length and the head portion is around 10 to 12 mm in width.

In this embodiment the medicament is contained or absorbed by or coated onto the head portion of the device such that it can be released over time into the vaginal cavity. Any suitable pharmaceutical means may be used to carry the drug and enable its release over time to the vaginal cavity.

Drugs which may be used to treat bacterial vaginosis include Flagyl (also known as Metronidazole), acidifiers to decrease pH to less than 5, less than 4.5, prebiotics, and probiotics. Other treatments include cleocin, ampicillin, ceftriaxone and tetracycline. Other drugs suitable for treating bacterial vaginosis such as pH regulators, suitable antibiotics and other drugs will be known to those skilled in the art.

The location of the implant in the smooth muscle myometrium of the cervix and/or part of the body of the smooth muscle myometrium of the uterus allows the implant to be easily inserted. During retention of the implant in the myometrium of the cervix, straightforward examination of the vaginal cavity 34 by a medical practitioner can verify that the implant is in its intended position in the myometrium. Whilst there is little chance of the implant becoming displaced, as the retrieval means, for example the cord or hook and in particular embodiments the head portion remains outside the myometrium, any such displacement can be easily observed.

Various improvements and modifications may be made without departing from the scope of the present invention. For example, as detailed above the body of the implant may be formed from absorbable polymers. This would avoid the need to remove the implant at a later date. Any suitable retrieval means can be provided on the implant to allow the implant to be moved into and out of the tissue of the myometrium or prostate.

What is claimed is:

1. An implantable delivery device system for delivery of a medicament to a bladder, the device comprising:
   a device body including a first end and a second end opposite of the first end, the first end having a first diameter and including a sharp tip for penetrating tissue and the second end having a second diameter and including a head portion, the second diameter is larger than the first diameter;
   a drug coating disposed over at least a portion of the device body, wherein the drug coating is provided for treatment of an over active bladder with controlled delivery of a drug over a duration of time; and
   an insertion tool, the insertion tool comprising a shaft located between a proximal end of the tool that includes a handle shaft and a distal end of the tool that is attachable to the head of the device.

2. The system of claim 1, wherein the device body includes a retrieval mechanism.

3. The system of claim 1, wherein the drug coating includes an anti-cholinergic drug.

4. The system of claim 1, wherein the drug coating includes a calcium antagonist.

5. The system of claim 1, wherein the drug coating includes an agent for radiotherapy.

6. The system of claim 1, wherein the device body is absorbable.

7. An implantable delivery device system for treatment of a bladder, the device comprising:
   a device body including a first end and a second end opposite of the first end, the first end having a first diameter and including a sharp tip configured to penetrate tissue of the bladder and the second end having a second diameter and including a head portion, the second diameter is larger than the first diameter;
   a medicament disposed over at least a portion of the device body, wherein the medicament is selected to treat the bladder through a controlled delivery of a therapeutic agent over a duration of time; and
   an insertion tool, the insertion tool comprising a shaft located between a proximal end of the tool that includes a handle shaft and a distal end of the tool that is attachable to the head of the device.

8. The system of claim 7, wherein the device body includes a retrieval mechanism.

9. The system of claim 7, wherein the medicament is selected to treat an over active bladder.

10. The system of claim 9, wherein the medicament includes an anti-cholinergic drug.

11. The system of claim 9, wherein the medicament includes a calcium antagonist.

12. The system of claim 9, wherein the medicament includes an agent for radiotherapy.

13. The system of claim 7, wherein the therapeutic agent is selected from the group consisting of anti-infectives, antimicrobials, prebiotics, probiotics, acidifiers, antivirals, antibiotics, anti-allergenics, anti-inflammatories, anti-fungals, anti-cholinesterases, and chemotherapeutic agents.

14. The system of claim 7, wherein the head portion is configured for manipulation and surveillance of the device body.

* * * * *